United States Patent [19]

Koster et al.

[11] Patent Number: 4,478,749

[45] Date of Patent: Oct. 23, 1984

[54] 2-OXO-1-(SUBSTITUTED PHOSPHOROUS)AZETIDINES

[75] Inventors: William H. Koster, Ringoes; Christopher M. Cimarusti, Pennington, both of N.J.

[73] Assignee: E. R. Squibb & Sons, Inc., Princeton, N.J.

[21] Appl. No.: 358,140

[22] Filed: Mar. 15, 1982

Related U.S. Application Data

[63] Continuation-in-part of Ser. No. 248,929, Mar. 30, 1981, abandoned.

[51] Int. Cl.$^3$ .................... C07D 205/08; C07F 9/65; C07F 9/58; A61K 31/675
[52] U.S. Cl. ........................... 260/245.4; 260/239 A; 260/330.3; 260/330.9; 544/232; 544/243; 544/337; 546/22; 424/200
[58] Field of Search ......... 260/239 A, 245.4, 343.3 R, 260/330.3, 330.9; 544/232, 243, 337; 546/22

[56] References Cited

U.S. PATENT DOCUMENTS 4,207,234  6/1980  Kamiya et al. ................ 260/239 A

FOREIGN PATENT DOCUMENTS 857284   1/1978  Belgium .
21678    1/1981  European Pat. Off. .
55-72813 7/1980  Japan .

OTHER PUBLICATIONS

Clauss et al., Justus Liebigs Ann. Chem., 4:539–560, (1974).
Campbell et al., J. Chem. Soc., Chem. Comm., 15:730–731, (1980).
Zamboni et al., Can. J. Chem., 57:1945–1948, (1979).
Saldabols, Isv. Akad. Nauk SSSR, Otd. Khim. Nauk 1495, (1962), (Chemical Abstracts 58:2418e).
Grechkin et al., Dokl. Akad. Nauk SSSR 162:1063–1064, (1965), (Chemical Abstracts 63:6939e).
Grechkin et al., Zh. Obshch. Khim., 36:1862, (1966), (Chemical Abstracts 66:55295t).
Gray et al., J. Org. Chem., 44:1768–1771, (1979).
Buchanan, Can. J. Chem., 57:21–26, (1979).
Grechkin, Dokl. Akad. Nauk SSSR, 172:1099–1101, (1967), (Chemical Abstracts 66:115768m).

*Primary Examiner*—Mark L. Berch
*Attorney, Agent, or Firm*—Lawrence S. Levinson; Donald J. Barrack

[57] ABSTRACT

Antibacterial activity is exhibited by β-lactams having a phosphinic or phosphonic substituent in the 1-position and an acylamino substituent in the 3-position.

24 Claims, No Drawings

2-OXO-1-(SUBSTITUTED PHOSPHOROUS)AZETIDINES

This is a continuation-in-part of U.S. patent application Ser. No. 248,929, filed Mar. 30, 1981, and now abandoned.

RELATED APPLICATIONS

U.S. patent application Ser. No. 226, 562, filed Jan. 10, 1981, discloses β-lactam antibiotics having a sulfonic acid salt (—SO₃⊕M⊕; M⊕ is a cation) in the 1-position and an acylamino substituent in the 3-position.

U.S. patent application Ser. No. 202,830, filed Oct. 31, 1980, now U.S. Pat. No. 4,337,197, issued Jun. 29, 1982 discloses β-lactam antibiotics having a sulfate (—O—SO₃⊕M⊕; M⊕ is a cation) substituent in the 1-position and an acylamino substituent in the 3-position.

BACKGROUND OF THE INVENTION
The β-lactam ring,

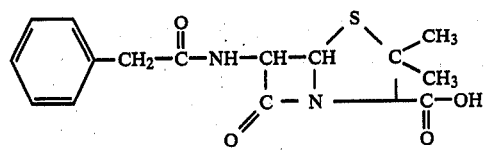

has been known since the late nineteenth century. While knowledge of β-lactam chemistry developed during the early 1900's, it was not until 1929 that Fleming reported in *Brit. J. Exper. Pathol.*, 10, 226 (1929) that a fermentation product of the organism *Penicillium notatum* had antibiotic properties. The compound which Fleming had worked with was benzylpenicillin,

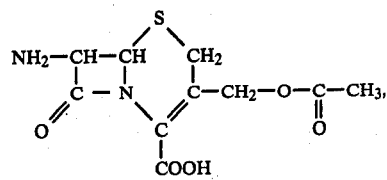

The in vivo activity of benzylpenicillin against various bacteria was reported by Chain et al. in *Lancet*, 2:226 (1940).

During the early 1940's research in the field of penicillins was intense. This research focused first on structure elucidation and then on synthetic routes for preparing benzyl penicillin. It was not, however, until the late 1950's that a totally synthetic route was discovered for the preparation of benzyl penicillin.

U.S. Pat. No. 2,941,955, issued Jun. 21, 1960, to Doyle et al., discloses the discovery of 6-aminopenicillanic acid,

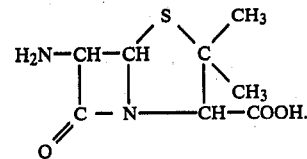

This patent was followed by U.S. Pat. No. 2,951,839, issued Sept. 6, 1960, also to Doyle et al., which discloses the use of 6-aminopenicillanic acid as a valuable intermediate which could be acylated, using art-recognized procedures, to obtain penicillin derivatives having antibiotic properties. Using 6-aminopenicillanic as a stepping stone, research chemists have prepared numerous penicillin derivatives having antibiotic activity.

The second major class of β-lactam antibiotics is the cephalosporins. In the 1940's a Cephalosporium species was found to produce an antibiotic that had activity against gram-positive and gram-negative bacteria. Work in the 1950's showed that the fermentation product of a Cephalosporium species contained not one, but several antibiotics. One of these antibiotics, cephalosporin C,

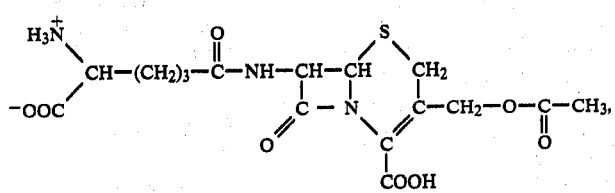

proved to be an important stepping stone in cephalosporin research. Removal of the acyl group in the 7-position of cephalosporin C yields 7-aminocephalosporanic acid, NH₂—CH—CH   S   CH₂
         C—N     C—CH₂—O—C—CH₃,
        O         C         O
                 COOH an intermediate useful for the preparation of numerous acylated compounds which are analogs of cephalosporin C.

The penicillins and cephalosporins are, of course, the most important of the β-lactam antibiotics reported to date. Others have, however, been reported. Stapley et al., *Antimicrobial Agents and Chemotherapy*, 2(3):122 (1972) disclose that certain actinomycete cultures isolated from soil produce antibiotics characterized by a methoxy group and D-α-aminoadipic acid on the 7-carbon of the cephem nucleus. The cephamycins, as they are known, have the formula

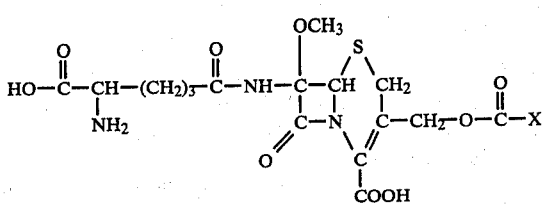

-continued cins, nocardicin A and B, are monocyclic β-lactams having the formula

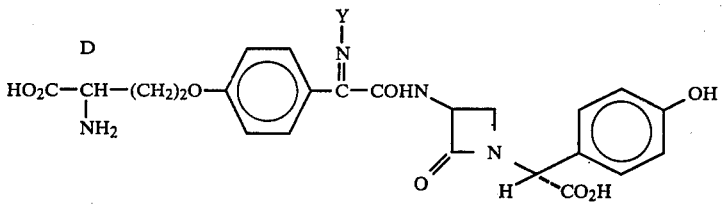

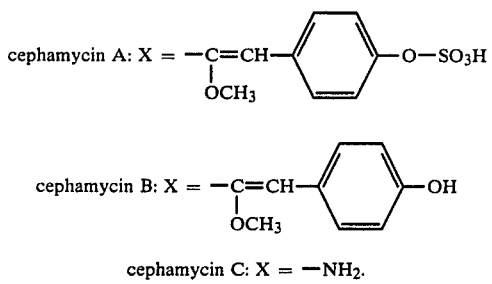

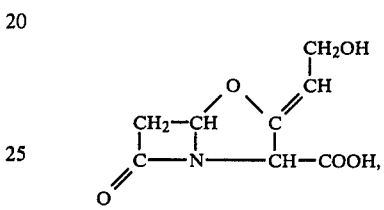

Stapley et al. reported that cephamycin A and cephamycin B each exhibits a similar range of potencies against gram-negative and gram-positive bacteria, and cephamycin C had greater potency against gram-negative bacteria than against gram-positive bacteria. Cephamycin C was reported to be the most active of the three antibiotics.

Scannell et al., The Journal of Antibiotics, XXVIII (1):1 (1975), disclose the isolation from a fermentation broth of Streptomyces species 372A of (S)-alanyl-3-[α-(S)-chloro-3-(S)-hydroxy-2-oxo-3-azetidinyl-methyl]-(S)-alanine, which has the formula

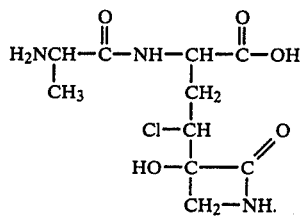

The structure of the above naturally occurring monocyclic β-lactam containing molecule is similar to the structure of the earlier discovered β-lactam containing molecules known as tabotoxins, i.e.,

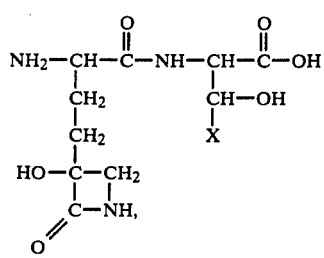

wherein X is hydrogen or methyl as reported by Stewart, Nature, 229:174 (1971), and Taylor et al., Biochem. Biophys. Acta., 286:107 (1972).

Recently, several novel series of naturally occurring β-lactam antibiotics have been isolated. The nocardias reported by Hashimoto et al., The Journal of Antibiotics, XXIX (9):890 (1976).

Clavulanic acid, a bicyclic β-lactam antibiotic isolated from fermentation broths of Streptomyces clavuligerus, has the formula

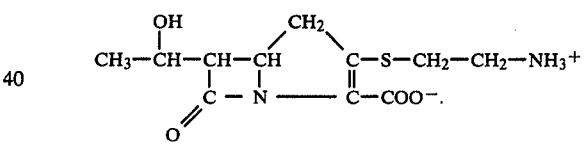

i.e., Z-(2R,5R)-3-(β-hydroxyethylidene)-7-oxo-4-oxa-1-azabicyclo[3,2,0]heptane-2-carboxylic acid, as reported by Lloyd et al., J. C. S. Chem. Comm., 266 (1976).

Still another recently isolated β-lactam antibiotic is thienamycin, an antibiotic isolated from the fermentation broths of Streptomyces cattleya. As reported by Albers-Schonberg et al., J. A. C. S., 100:20, 6491 (1978), thienamycin has the structure

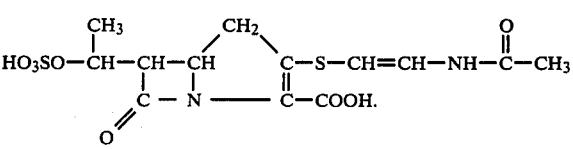

Additional fused β-lactams, olivanic acid derivatives, have recently been isolated from cultures of Streptomyces olivaceus. As disclosed by Brown et al., J. C. S. Chem. Comm., these olivanic acid derivatives have the formulas

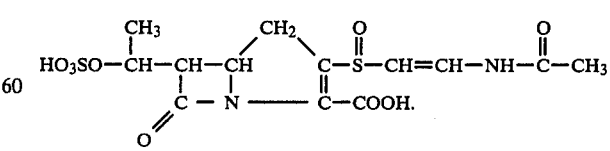

and

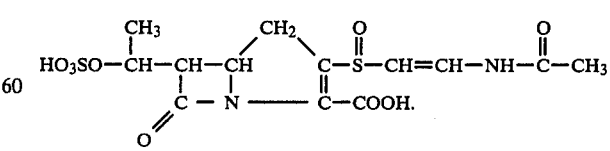

The isolation of the above antibiotics, and a discussion of their activity, is reported by Butterworth et al., The Journal of Antibiotics, XXXII (4):294 (1979) and by Hood et al., The Journal of Antibiotics, XXXII (4):295 (1979).

Another recently isolated β-lactam antibiotic is PS-5, reported by Okamura et al., *The Journal of Antibiotics*, XXXI: 480 (1978) and *The Journal of Antibiotics*, XXXII (4):262 (1979). The structure of this antibiotic, which is produced by *Streptomyces cremeus* subspecies *auratilis*, is reported to be $$CH_3-CH_2-CH-CH \underset{\underset{O}{\overset{\|}{C}}-N}{\overset{CH_2}{\diagdown}} \underset{C-COOH}{\overset{\|}{C}}-S-CH_2-CH_2-NH-\overset{O}{\overset{\|}{C}}-CH_3$$

Structurally related antibiotics PS-6 and PS-7 are reported in European patent application Ser. No. 1,567 to have the respective structures $$\underset{CH_3}{\overset{CH_3}{\diagdown}}CH-CH-CH \underset{\underset{O}{\overset{\|}{C}}-N}{\overset{CH_2}{\diagdown}} \underset{C-COOH}{\overset{\|}{C}}-S-CH_2-CH_2-NH-\overset{O}{\overset{\|}{C}}-CH_3$$

and $$CH_3-CH_2-CH-CH \underset{\underset{O}{\overset{\|}{C}}-N}{\overset{CH_2}{\diagdown}} \underset{C-COOH}{\overset{\|}{C}}-S-CH=CH-NH-\overset{O}{\overset{\|}{C}}-CH_3$$

BRIEF DESCRIPTION OF THE INVENTION

This invention is directed to a novel family of β-lactam antibiotics, and to the use of such compounds as antibacterial agents. It has been discovered that the β-lactam nucleus can be biologically activated by a substituent having the formula $$-\overset{O}{\overset{\|}{P}}\diagdown_{R_6}^{OR_5}$$

attached to the nitrogen atom in the nucleus.

β-Lactams having a $$-\overset{O}{\overset{\|}{P}}\diagdown_{R_6}^{OR_5}$$

substituent in the 1-position and an acylamino substituent the 3-position (and salts thereof) exhibit activity against a range of gram-negative and gram-positive bacteria.

Illustrative members of the novel family of β-lactam antibiotics of this invention are those encompassed by the formula $$R_1-NH-\overset{\underline{R_2}}{\overset{\|}{C}}-\overset{\underline{R_4}}{\overset{\|}{C}}-R_3 \atop \underset{O}{\overset{\diagup}{C}}-N-\overset{O}{\overset{\|}{P}}\diagdown_{R_6}^{OR_5}$$

I and salts thereof.

In addition to the above described β-lactams having a $$-\overset{O}{\overset{\|}{P}}\diagdown_{R_6}^{OR_5}$$

substituent in the 1-position and an acylamino substituent in the 3-position, this invention also encompasses β-lactams having a $$-\overset{O}{\overset{\|}{P}}\diagdown_{R_6}^{OR_5}$$

substituent in the 1-position and an amino substituent in the 3-position.

Illustrative compounds of this type have the formula $$NH_2-\overset{\underline{R_2}}{\overset{\|}{C}}-\overset{\underline{R_4}}{\overset{\|}{C}}-R_3 \atop \underset{O}{\overset{\diagup}{C}}-N-\overset{O}{\overset{\|}{P}}\diagdown_{R_6}^{OR_5}$$

II

These compounds are intermediates useful for the preparation of corresponding 3-acylamino compounds.

As used in formulas I and II, and throughout the specification, the symbols are as defined below.

$R_1$ is acyl;

$R_2$ is hydrogen or methoxy;

$R_3$ and $R_4$ are the same or different and each is hydrogen, alkyl, cycloalkyl, phenyl or substituted phenyl, or one of $R_3$ and $R_4$ is hydrogen and the other is alkoxycarbonyl, alken-1-yl, alkyn-1-yl, 2-phenylethenyl, 2-phenylethynyl, carboxyl, $-CH_2X_1$ (wherein $X_1$ is azido, amino ($-NH_2$), hydroxy, alkanoylamino, alkylsulfonyloxy, phenylsulfonyloxy, (substituted phenyl)sulfonyloxy, phenyl, substituted phenyl, halogen, benzylthio,(substituted phenyl)methylthio, triphenylmethylthio, cyano or mercapto), $-S-X_2$ or $-O-X_2$ (wherein $X_2$ is alkyl, phenyl, substituted phenyl, alkanoyl, phenylcarbonyl, (substituted phenyl)carbonyl, or heteroarylcarbonyl), or $$-O-\overset{X_3}{\underset{X_5}{\overset{|}{C}}}-X_4 \text{ or } -S-\overset{X_3}{\underset{X_5}{\overset{|}{C}}}-X_4$$

(wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl,

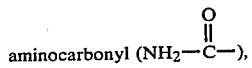
aminocarbonyl ($NH_2-\overset{\overset{O}{\|}}{C}-$), (substituted amino)carbonyl, or cyano ($-C\equiv N$));

$R_5$ is hydrogen, alkyl, substituted alkyl, phenyl, or substituted phenyl; and $R_6$ is hydroxy, alkoxy, (substituted alkyl)oxy, phenyloxy, (substituted phenyl)oxy, alkyl, substituted alkyl, phenyl, substituted phenyl, heteroaryl, amino($-NH_2$), substituted amino, alkylthio, (substituted alkyl)thio, phenylthio, (substituted phenyl)thio, 1-(ethoxycarbonyloxy)-ethoxy, 1,3-dihydro-3-oxo-1-isobenzofuranyloxy,

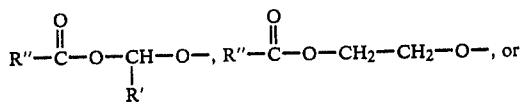

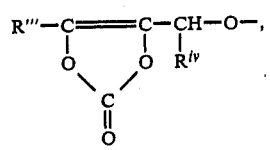

wherein $R'$ is hydrogen or alkyl, $R''$ is alkyl or phenyl, $R'''$ is hydrogen, methyl or phenyl, and $R^{iv}$ is hydrogen or together with $R'''$ is $-(CH_2)_3-$ or $-(CH_2)_5-$.

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The term "substituted alkyl" refers to alkyl groups substituted with one, or more, azido, amino($-NH_2$), halogen, hydroxy, carboxy, cyano, alkoxycarbonyl, aminocarbonyl, alkoxy, phenyloxy, (substituted phenyl)oxy, (heteroaryl)oxy, mercapto, alkylthio, phenylthio, (substituted phenyl)-thio, alkylsulfinyl, or alkylsulfonyl groups.

The terms "alkanoyl", "alkenyl", "alken-1-yl" and "alkyn-1-yl" refer to both straight and branched chain groups. Those groups having 2 to 10 carbon atoms are preferred.

The term "halogen" refers to fluorine, chlorine, bromine and iodine.

The term "protected carboxyl" refers to a carboxyl group which has been esterified with a conventional acid protecting group. These groups are well known in the art; see, for example, U.S. Pat. No. 4,144,333, issued Mar. 13, 1979. The preferred protected carboxyl groups are benzyl, benzhydryl, t-butyl, and p-nitrobenzyl esters.

The term "substituted phenyl" refers to a phenyl group substituted with 1, 2 or 3 amino($-NH_2$), halogen, hydroxyl, trifluoromethyl, alkyl (of 1 to 4 carbon atoms), alkoxy (of 1 to 4 carbon atoms), or carboxyl groups.

The term "heteroaryl" refers to a 5-, 6- or 7-membered heterocyclic aromatic ring containing 1,2,3 or 4 (preferably 1 or 2) nitrogen, oxygen and sulfur atoms, and to such rings substituted with one or more halogen, hydroxyl, nitro, amino, cyano, trifluoromethyl, alkyl (of 1 to 4 carbon atoms) or alkoxy (of 1 to 4 carbon atoms) groups. Exemplary heteroaryl groups are thienyl, furyl, pyrrolyl, pyridinyl, pyrazolyl, pyrazinyl, thiazolyl, pyrimidinyl and tetrazolyl.

The term "substituted amino" refers to a group having the formula $-NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl) alkyl, hydroxy, cyano, alkoxy, phenylalkoxy, or amino ($-NH_2$), or $Y_1$ and $Y_2$ together with the nitrogen atom to which they are attached form a 5,6, or 7-membered fully or partially saturated ring optionally containing additional nitrogen, oxygen or sulfur atoms.

The term "acyl" includes all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, Cephalosporins and Penicillins, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_7$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

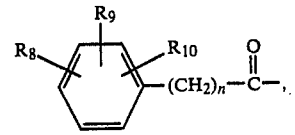

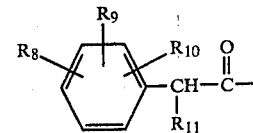

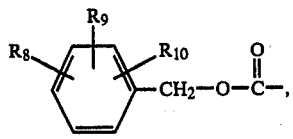

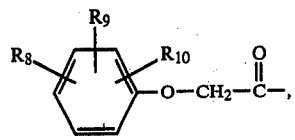

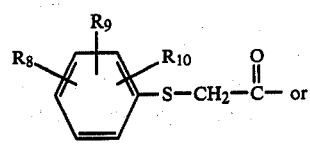

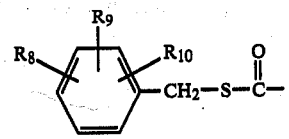

wherein n is 0, 1, 2 or 3; $R_8$, $R_9$, and $R_{10}$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_{11}$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

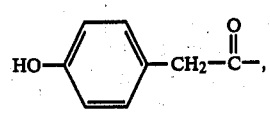

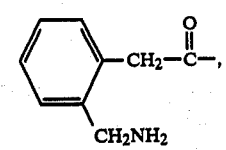

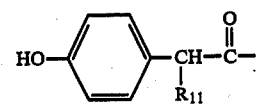

($R_{11}$ is preferbly a carboxyl salt or sulfo salt) and

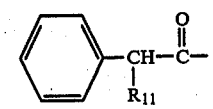

($R_{11}$ is preferably a carboxyl salt or sulfo salt).

(c) Heteroaromatic groups having the formula

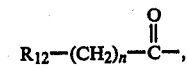

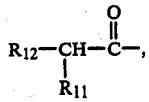

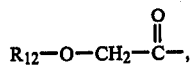

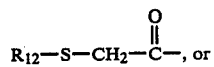

wherein n is 0, 1, 2 or 3; $R_{11}$ is as defined above; and $R_{12}$ is a substituted or unsubstituted 5-, 6- or 7-membered heterocyclic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, morpholinyl, pyrimidinyl and tetrazolyl. Exemplary substituents are halogen, hydroxyl, nitro, amino, cyano, trifluoromethyl, alkyl of 1 to 4 carbon atoms, alkoxy of 1 to 4 carbon atoms, or

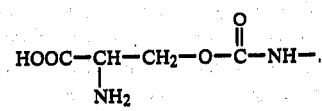

Preferred heteroaromatic acyl groups include those groups of the above formulas wherein $R_{12}$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)-carbonyl]amino]arylacetyl groups having the formula

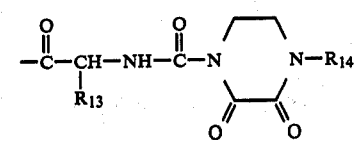

wherein $R_{13}$ is an aromatic group (including carbocyclic aromatics such as those of the formula

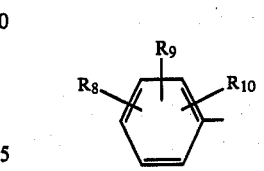

and heteroaromatics as included within the definition of $R_{12}$); and $R_{14}$ is hydrogen, alkyl, substituted alkyl (wherein the alkyl group is substituted with one or more halogen, cyano, nitro, amino or mercapto groups), arylmethyleneamino (i.e., $-N=CH-R_{13}$ wherein $R_{13}$ is as defined above), arylcarbonylamino (i.e.,

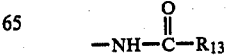

wherein $R_{13}$ is as defined above) or alkylcarbonylamino.

Preferred [[(4-substituted-2,3-dioxo-1-piperazinyl)-carbonyl]amino]arylacetyl groups include those wherein $R_{14}$ is ethyl, phenylmethyleneamino or 2-furylmethyleneamino.

(e) (Substituted oxyimino)arylacetyl groups having the formula

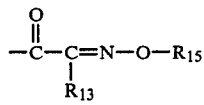

wherein $R_{13}$ is as defined above and $R_{15}$ is hydrogen, alkyl, cycloalkyl, alkylaminocarbonyl, arylaminocarbonyl (i.e.,

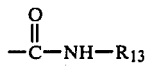

wherein $R_{13}$ is as defined above) or substituted alkyl (wherein the alkyl group is substituted with 1 or more halogen, cyano, nitro, amino, mercapto, alkylthio, aromatic group (as defined by $R_{13}$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy (phenylmethoxy)phosphinyl, or dialkoxyphosphinyl substituents).

Preferred (substituted oxyimino)arylacetyl groups include those wherein $R_{13}$ is 2-amino-4-thiazolyl. Also preferred are those groups wherein $R_{15}$ is methyl, ethyl, carboxymethyl, 1-carboxy-1-methylethyl, 2,2,2-trifluoroethyl or 2-carboxycyclopropyl.

(f) (Acylamino)arylacetyl groups having the formula

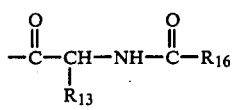

wherein $R_{13}$ is as defined above and $R_{16}$ is

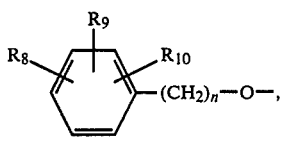

amino, alkylamino, (cyanoalkyl)amino, amido, alkylamido, (cyanoalkyl)-amido,

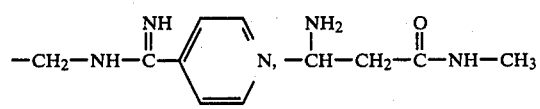

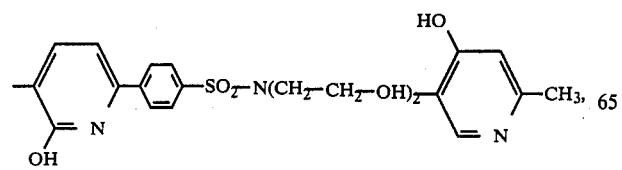

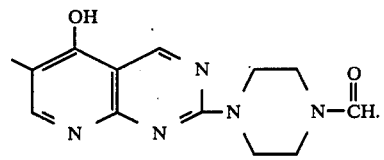

Preferred (acylamino)arylacetyl groups of the above formula include those groups wherein $R_{16}$ is amino or amido. Also preferred are those groups wherein $R_{13}$ is phenyl or 2-thienyl.

(g) [[[3-Substituted-2-oxo-1-imidazolidinyl]carbonyl]amino]arylacetyl groups having the formula

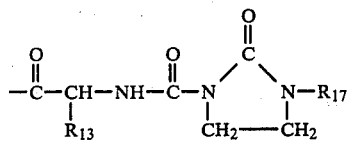

wherein $R_{13}$ is as defined above and $R_{17}$ is hydrogen, alkylsulfonyl, arylmethyleneamino (i.e., $-N=CH-R_{13}$ is as defined above),

(wherein $R_{18}$ is hydrogen, alkyl or halogen substituted alkyl), aromatic group (as defined by $R_{13}$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_{13}$ is phenyl or 2-thienyl. Also preferred are those groups wherein $R_{17}$ is hydrogen, methylsulfonyl, phenylmethyleneamino or 2-furylmethyleneamino.

The compounds of this invention form basic salts with various inorganic and organic bases which are also within the scope of this invention. Such salts include ammonium salts, alkali metal salts, alkaline earth metal salts, salts with organic bases, e.g., dicyclohexylamine, benzathine, N-methyl-D-glucamine, hydrabamine and the like. The pharmaceutically acceptable salts are preferred, although other salts are also useful, e.g., in isolating or purifying the product.

Some of the compounds of this invention may be crystallized or recrystallized from solvents containing water. In these cases water of hydration may be formed. This invention contemplates stoichiometric hydrates as well as compounds containing variable amounts of water that may be produced by processes such as lyophilization.

β-Lactams having a

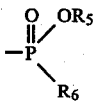

substituent in the 1-position and an amino or acylamino substituent in the 3-position contain at least one chiral center —the carbon atom (in the 3-position of the β-lactam nucleus) to which the amino or acylamino substituent is attached. The invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C).

With respect to the preferred β-lactams of formulas I and II, the structural formulas have been drawn to show the stereochemistry at the chiral center in the 3-position.

Also included within the scope of this invention are racemic mixtures which contain the above-described β-lactams.

DETAILED DESCRIPTION OF THE INVENTION

β-Lactams having a

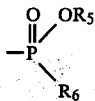

substituent in the 1-position of the β-lactam nucleus and an acylamino substituent in the 3-position of the β-lactam nucleus, and salts thereof, have activity against a range of gram-negative and gram-positive organisms.

The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular, and as a suppository.

The β-lactam antibiotics of this invention can be prepared from the corresponding azetidinone having the formula

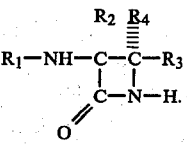

III

If the acyl group ($R_1$) in a compound of formula III contains reactive functionality (such as hydroxyl, amino, or carboxyl groups) it may be necessary to first protect those functional groups, then proceed with the synthetic procedures described below, and finally deprotect the resulting product.

Phosphorylation of an azetidinone of formula III can be accomplished by first converting the azetidinone to a salt having the formula

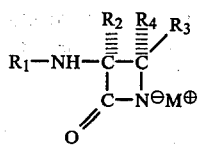

IV ($M^\oplus$ is a cation) by reaction with a strong base, and then reacting the salt with an activated phosphorous derivative having the formula

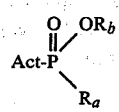

V (Act is an activating group, e.g., a halogen atom, $R_b$ is alkyl, substituted alkyl, phenyl, or substituted phenyl, and $R_a$ is alkoxy, (substituted alkyl)oxy, phenyloxy, (substituted phenyl)oxy, alkyl, substituted alkyl, phenyl, substituted phenyl, heteroaryl, alkylthio, (substituted alkyl)thio, phenylthio, (substituted phenyl)thio, or $$R''-\overset{O}{\overset{\|}{C}}-O-CH_2-CH_2-O-$$

to yield compounds having the formula

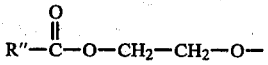

VI

Alternatively, phosphorylation of an azetidinone of formula III can be accomplished by first silylating an azetidinone of formula III to yield a compound having the formula

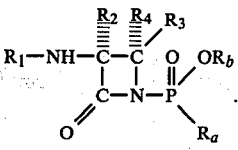

VII wherein X, Y and Z are alkyl, phenyl, or substituted phenyl; preferably X, Y and Z are each methyl. Among the silylating agents which are useful in the above reaction are trimethylsilyl chloridetriethylamine and bis-(trimethylsilyl)trifluoroacetamide. Reaction of a silylated azetidinone of formula VII with an activated phosphorous residue of formula V yields the corresponding compound of formula VI.

Still another method for the phosphorylation of an azetidinone of formula III comprises first halogenating an azetidinone of formula III to yield a compound of the formula

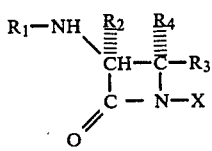  VIII (X is halogen). The Michaelis-Arbusov reaction of a compound of formula VIII with a trivalent phosphorous derivative having the formula

  IX ($R_c$ is alkyl, substituted alkyl, phenyl, substituted phenyl, alkoxy, (substituted alkyl)oxy, phenyloxy, or (substituted phenyl)oxy and $R_d$ is alkyl) yields the corresponding compound having the formula

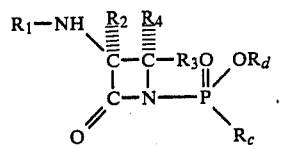  X

Still another method for the phosphorylation of an azetidinone of formula III comprises first converting the azetidinone to a salt of formula IV and then reacting the salt with a phosphorous derivative having the formula

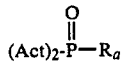  XI wherein the activating group "Act" is, most preferably, chlorine to yield compounds having the formula

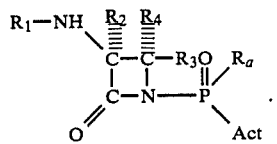  XII

The compounds of formula XII are useful intermediates, and as such, form an integral part of this invention.

Reaction of an intermediate of formula XII with ammonia or an amine having the formula

 HNY₁Y₂  XIII displaces the activating group ("Act") and yields the corresponding compound of formula I having the formula

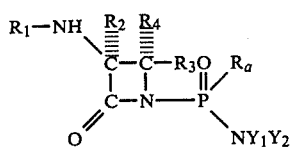  XIV

Reaction of an intermediate of formula XII with an alkanol or mercaptan having the formula

 $R_b$—ZH,  XV wherein Z is oxygen or sulfur, or with water, displaces the activating group ("Act") and yields the corresponding compound having the formula

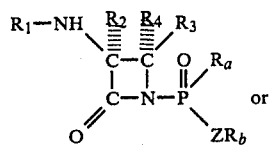  XVI or

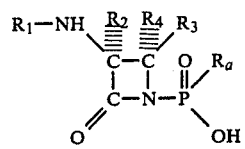  XVII

Mono-acidic phosphorous derivatives can also be obtained from the corresponding mono- or dialkyl esters having the formula

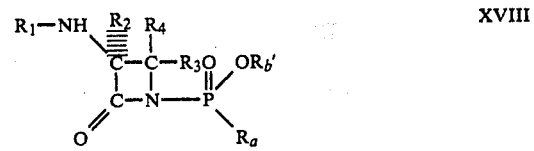  XVIII wherein $R_b'$ methyl, ethyl or n-propyl. Heating a compound of formula XVIII with thiourea in acetonitrile yields a thiuronium salt of a compound of formula XVII, which upon treatment with a cationic ion exchange resin yields a different salt of a compound of formula XVII. Alternatively, treatment of a compound of formula XVIII with a tetralkylammonium halide yields a tetraalkylammonium salt of a compound of formula XVII, which upon treatment with a cationic ion exchange resin yields a different salt of a compound of formula XVII.

Alternatively, mono-acidic phosphorous derivatives can be obtained from the corresponding mono- or dialkyl esters of formula XVIII by treatment with an acid-scavenger and drying agent such as bis-trimethylsilylacetamide followed by treatment with trimethylsilyl bromide to yield an intermediate silyl ester having the formula

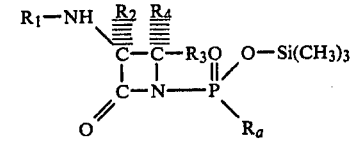  XIX

An intermediate of formula XIX is readily converted to a salt of the corresponding compound of formula XVII by treatment with an organic or inorganic base in the presence of water or an alcohol.

The tetralkylammonium salt of a compound of formula XVII can be treated with an alkyl halide, (substituted alkyl)halide, 1-(ethoxycarbonyloxy)ethyl halide, 1,3-dihydro-3-oxo-1-isobenzofuranyl halide,

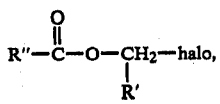

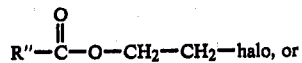

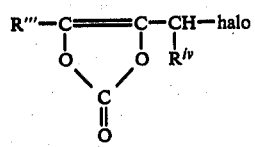

to obtain an ester having the formula

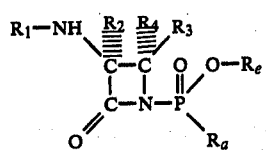 XX wherein $R_e$ is alkyl, substituted alkyl, 1-(ethoxycarbonyloxy)ethyl, 1,3-dihydro-3-oxo-1-isobenzofuranyl,

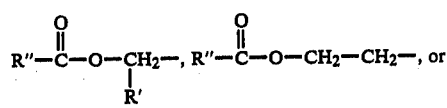

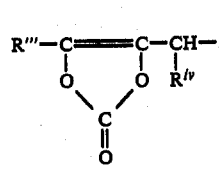

When $R_a$ is methoxy or ethoxy, this process results in transesterification, yielding the tetraalkylammonium salt of a compound having the formula

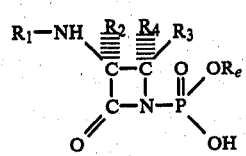 XXI

A compound of formula XXI can be converted to the corresponding compound of formula XX wherein $R_a$ is methoxy or ethoxy by treating the tetralkylammonium salt of the compound of formula XXI with methyl or ethyl sulfate. Alternatively, the tetraalkylammonium salt of the compound of formula XXI can be converted to the corresponding acid on ion-exchange resin and then treated with diazomethane or diazoethane to yield the desired compound of formula XX wherein $R_a$ is methoxy or ethoxy.

A process for obtaining diacidic phosphorous derivatives comprises utilization of a dialkyl ester having the formula

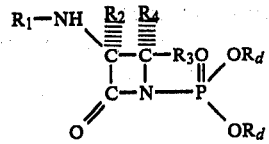 XXII (corresponds to compound of formula X wherein $R_{hd\ c}$ is alkoxy). Treatment of a dialkyl ester of formula XXII with an acid-scavenger and drying agent such as bis-trimethylsilylacetamide followed by treatment with at least two equivalents of trimethylsilyl bromide yields an intermediate having the formula

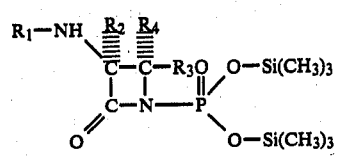 XXIII

An intermediate of formula XXIII is readily converted to a salt of the corresponding compound having the formula

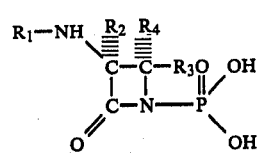 XXIV by treatment with an organic or inorganic base in the presence of water or an alcohol.

Products of formula I wherein $R_1$ is a readily cleavable acyl group, can be used to prepare other compounds of formula I. If, for example, a compound of formula I wherein $R_1$ is benzyloxycarbonyl is catalytically hydrogenated, or a compound of formula I wherein $R_1$ is t-butoxycarbonyl is treated with acid, an intermediate having the formula

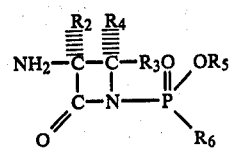 II is obtained.

Well known acylation techniques can be used to convert an intermediate of formula II to a corresponding product of formula I. Exemplary techniques include reaction of a compound of formula II with a carboxylic acid ($R_1$—OH), or corresponding carboxylic acid halide, or carboxylic acid anhydride or mixed anhydride. The reaction with a carboxylic acid proceeds most readily in the presence of a carbodiimide such as dicyclohexylcarbodiimide and a substance capable of forming an active ester in situ such as N-hydroxybenzotriazole. In those instances wherein the acyl group ($R_1$) or $R_3$, $R_4$ or $R_6$ groups contain reactive functionality (such as amino or carboxyl groups) it may be necessary to first protect those functional groups, then carry out the acylation reaction, and finally deprotect the resulting product.

The starting azetidinones of formula III are obtainable using any one of numerous procedures.

A compound of formula III can be obtained by first reacting an olefin having the formula

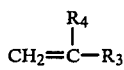   XXV with a halosulfonylisocyanate (preferably chlorosulfonylisocyanate) having the formula $O{=}C{=}N{-}SO_2{-}$halogen,   XXVI to yield an azetidinone having the formula

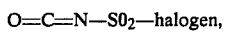   XXVII

Reductive hydrolysis of an azetidinone of formula XXVII yields an N-unsubstituted β-lactam having the formula

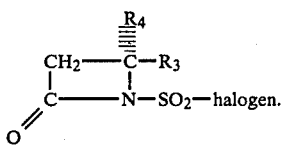   XXVIII

For a more detailed description of the above described reaction sequence reference can be made to the literature; see, for example, *Chem. Soc. Rev.*, 5, 181 (1976) and *J. Org. Chem.*, 35, 2043 (1970).

An azido group can be introduced in the 3-position of an azetidinone of formula XXVIII by reaction of the compound with an arylsulfonyl azide (such as toluenesulfonyl azide) to obtain an azetidinone having the formula

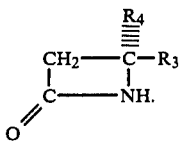   XXIX

The reaction proceeds best by first protecting the azetidinone nitrogen with a silyl residue (e.g., t-butyldimethylsilyl, or t-butyldiphenylsilyl), then generating the anion at the 3-position of the nucleus with a strong organic base (e.g., lithium diisopropylamine) at a low temperature, and then treating the anion with toluenesulfonyl azide. The resulting intermediate is quenched with trimethylsilyl chloride, and subsequent acid hydrolysis or fluoride solvolysis of the N-protecting group yields the compound of formula XXIX.

Reduction of a 3-azido-2-azetidinone of formula XXIX yields the corresponding compound having the formula

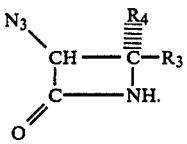   XXX

The reduction can be accomplished by catalytic (e.g., palladium on charcoal or platinum oxide) hydrogenation or with reducing agents such as zinc or triphenylphosphine.

Acylation of a 3-amino-2-azetidinone using art-recognized procedures described above yields the corresponding starting material of formula III wherein $R_2$ is hydrogen; i.e., a compound having the formula

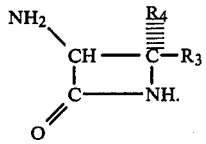   XXXI

The starting azetidines of formula III wherein $R_2$ is methoxy can be obtained from the corresponding non-methoxylated compound of formula XXXI, wherein $R_1NH$ is a carbamate (e.g., $R_1$ is benzyloxycarbonyl). Halogenation (preferably chlorination) of the amide nitrogen of such a compound yields a compound having the formula

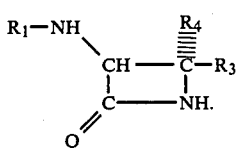   XXXII

Reagents and procedures for N-chlorinating amides are known in the art. Exemplary reagents are t-butyl hypochlorite, sodium hypochlorite, and chlorine. The reaction can be run in an organic solvent (e.g., a lower alkanol such as methanol) or a two phase solvent system (e.g., water/methylene chloride) in the presence of a base such as sodium borate decahydrate. The reaction is preferably run at a reduced temperature.

Reaction of a compound of formula XXXII with a methoxylating agent such as an alkali metal methoxide, followed by reaction with a reducing agent such as trimethylphosphite, yields a compound having the formula

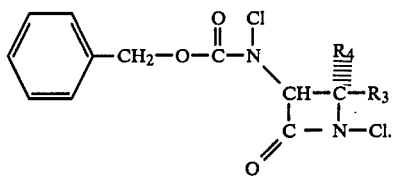   XXXIII in combination with its enantiomer if $R_3$ and $R_4$ are the same. If $R_3$ and $R_4$ are not the same, two optically active diastereomers are formed.

Catalytic hydrogenation of a compound of formula XXXIII, followed by acylation using art-recognized procedures yields the corresponding starting material of formula III wherein $R_2$ is methoxy; i.e., a compound having the formula

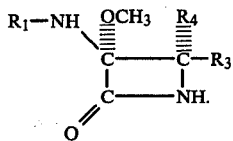   XXXIV

An alternative synthesis for the preparation of a starting material of formula III wherein $R_3$ and $R_4$ are each hydrogen utilizes a 6-acylaminopenicillanic acid having the formula

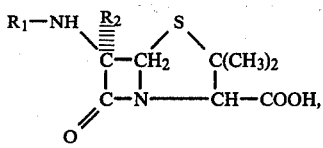   XXXV or a salt thereof, as the starting material. By adapting procedures described in the literature, 3-acylamino-2-azetidinone can be obtained from the corresponding 6-acylaminopenicillanic acid of formula XII: see, for example, Chem. Soc. Special Publication No. 28, pg. 288 (1977), The Chemistry of Penicillins, Princeton University Press, pg. 257, and Synthesis, 494 (1977).

As described in the literature 6-acylaminopenicillanic acid, or a salt thereof, can be desulfurized to yield a compound having the formula

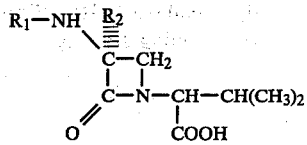   XXXVI by reduction using Raney nickel. The reaction can be run in water under reflux conditions.

Replacement of the carboxyl group of a compound of formula XXXVI with an acetate group followed by hydrolysis yields the corresponding 3-acylamino-2-azetidinone having the formula

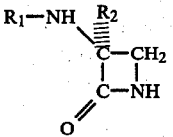   XXXVII

Treatment of a compound of formula XXXVI with cupric acetate and lead tetraacetate in an organic solvent (e.g., acetonitrile) replaces the carboxyl group with an acetate group. Hydrolysis of the resulting compound can be accomplished using potassium carbonate in the presence of sodium borohydride.

A variation of the above-described synthetic route for the preparation of a starting compound of formula III wherein $R_3$ and $R_4$ are each hydrogen comprises first desulfurizing 6-aminopenicillanic acid, acylating the resulting compound to yield a compound of formula XXXV and the proceeding as described above to obtain a 3-acylamino-2-azetidinone of formula XXXVII.

Alternatively, the above-described procedures can be carried out utilizing a 7-acylaminocephalosporanic acid in place of the 6-acylaminopenicillanic acid of formula XXXV.

The azetidinones of formula III wherein $R_2$ is hydrogen and at least one of $R_3$ and $R_4$ is hydrogen can also be prepared from amino acids having the formula

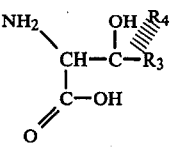   XXXVIII (at least one of $R_3$ and $R_4$ is hydrogen). The amino group is first protected (with a protecting group "A", e.g., t-butoxycarbonyl). The carboxyl group of the protected amino acid is then reacted with an amine having the formula $Y-O-NH_2$,   IXL wherein Y is alkyl or benzyl, in the presence of a carbodiimide to yield a compound having the formula

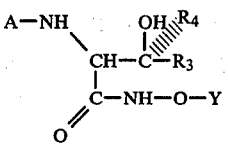   XL (at least one of $R_3$ and $R_4$ is hydrogen). The hydroxyl group of a compound of formula XL is converted to a leaving group with a classical reagent, e.g., methanesulfonyl chloride (methanesulfonyl is referred to hereinafter as "Ms").

The fully protected compound having the formula

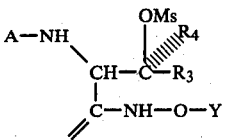   XLI (at least one of $R_3$ and $R_4$ is hydrogen) is cyclized by treatment with base, e.g., potassium carbonate. The reaction is preferably carried out in an organic solvent such as acetone, under reflux conditions, and yields a compound having the formula

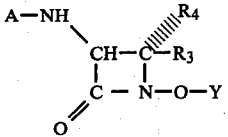   XLII (at least one of $R_3$ and $R_4$ is hydrogen).

Alternatively, cyclization of a compound of formula XL can be accomplished without first converting the hydroxyl group to a leaving group. Treatment of a compound of formula XL with triphenylphosphine and diethylazodicarboxylate, yields a compound of formula XLII wherein at least one of $R_3$ and $R_4$ is hydrogen.

Both of the methods disclosed above for ring closure of a compound of formula XL result in the inversion of the stereochemistry at the carbon atom bearing the $R_3$ and $R_4$ substituents.

Removal of the protecting group from the 1-position of an azetidinone of formula XLII can be accomplished via sodium reduction when Y is alkyl, and yields an intermediate having the formula

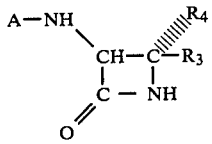   XLIII (at least one of $R_3$ and $R_4$ is hydrogen). If Y is benzyl, catalytic (e.g., palladium on charcoal) hydrogenation will initially yield the corresponding N-hydroxy compound, which upon treatment with titanium trichloride yields an intermediate of formula XLIII wherein at least one of $R_3$ and $R_4$ is hydrogen.

Deprotection of a compound of formula XLIII, followed by acylation using art-recognized procedures yields the corresponding starting material of formula III.

A 3-acylamino-2-azetidinone of formula III wherein $R_2$ and $R_4$ each is hydrogen can be prepared by first reacting a primary amine having the formula

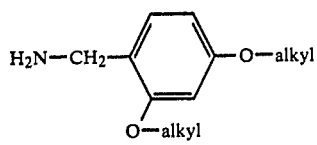   XLIVa or

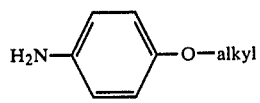   XLIVb with an aldehyde having the formula

   XLV (or a hemiacetal) to yield the corresponding Schiff base. A [2+2]cycloaddition reaction of the Schiff base with an activated form of α-azidoacetic acid yields a 3-azido-2-azetidinone having the formula

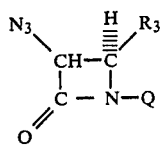   XLVI wherein Q is

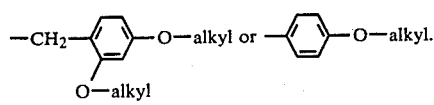

Oxidative removal of the 1-substituent yields the corresponding compound having the formula

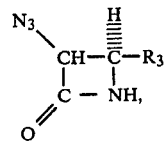   XLVII which can be reduced and acylated as described above to yield the desired starting material.

A compound of formula III wherein $R_4$ is hydrogen can be obtained using a procedure analogous to that described above for the preparation of a 3-azido-2-azetidinone of formula XLVI. In place of an activated form of α-azidoacetic acid, an activated form of α-phthalimidoacetic acid is used, yielding a compound having the formula

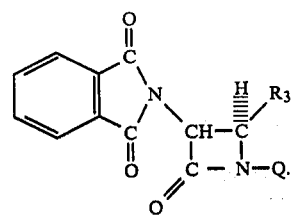   XLVIII

Reaction of a compound of formula XLVIII with a reagent such as methyl hydrazine (to cleave the phthaloyl group), followed by the introduction of a protecting group on the 3-nitrogen substituent, and oxidative removal of the 1-protecting group will yield a compound of formula XLIII wherein $R_4$ is hydrogen. Deprotection of a compound of formula XXIII, followed by acylation yields the corresponding starting material of formula III.

The following examples are specific embodiments of this invention.

EXAMPLE 1

(S)-[1-(Dimethoxyphosphinyl)-2-oxo-3-azetidinyl]carbamic acid, phenylmethyl ester Method I:

(S)-3-Benzyloxycarbonylamino-2-azetidinone (100 mg) was dissolved in dry tetrahydrofuran (2 ml), rapidly cooled to −78° C., and sec-butyl lithium (324 μl of 1.4N in cyclohexane) was added. After stirring for several minutes, dimethylphosphorochloridate (80 μl, 0.555 mmol) was added and the mixture was stirred at −78° C. for ½ hour. The reaction mixture was diluted with dichloromethane, washed with water, dried (sodium sulfate), filtered through Celite and solvent was removed in vacuo. The residual oil was chromatographed on two silica gel plates developed in ethyl acetate, yielding the product as an oil (95 mg) which crystallized from ethyl acetate, yielding 35 mg* of product, melting point 71.5°–73° C.

*A second crop was obtained from ether (30 mg. melting point 70°–72° C.).

Anal. Calc'd for $C_{13}H_{17}N_2O_6P$: C, 47.56; H, 5.22; N, 8.54; P, 9.44. Found: C, 47.84; H, 5.41; N, 8.65; P, 9.44.

Method II:

A suspension of (S)-3-benzyloxycarbonylamino-2-azetidinone (100 mg, 0.454 mmol) in carbon tetrachloride (2 ml) was refluxed with bis-trimethylsilyltrifluoroacetamide (241 μl 0.908 mmol) for 5 hours causing dissolution of the solid. Dimethylphosphorochloridate (200 μl) was added and, after refluxing overnight, the mixture was stirred at room temperature for 3 days. Removal of solvent in vacuo gave a crude oil, which after chromatography on preparative thin-layer silica gel plates yielded the desired product (61 mg).

Method III:

To a solution of (S)-3-benzyloxycarbonylamino-2-azetidinone (112 mg) in dry tetrahydrofuran (2 ml) cooled to −78° C. was added a solution of potassium t-butoxide (61 mg) in dry tetrahydrofuran (3 ml). The mixture was stirred under an inert atmosphere for 5 minutes, dimethylphosphorochloridate (80 ul)was added and stirring was continued for 35 minutes at −78° C. After diluting the reaction with dichloromethane, washing with diluted sodium chloride solution, and drying (sodium sulfate), the desired product was obtained (49 mg) by removal of solvent in vacuo and chromatography of the crude oil on preparative thin-layer silica gel plates.

Method IV:

A solution of (S)-3-benzyloxycarbonylamino-2-azetidinone (440 mg) in dichloromethane (15 ml) was combined with a solution of borax (1.53 g) in water (10 ml) and cooled in an ice-bath to 0°–5° C. While stirring vigorously, a 5.07% solution of sodium hypochlorite (3.2 ml) was added; after 1 hour another portion (1.6 ml) of hypochlorite solutionwas added and stirring was continued for 1 hour at 0°–5° C. The organic layer was separated and the aqueous solution was extracted with dichloromethane. The combined extracts were dried (sodium sulfate) and solvent was removed in vacuo giving (S)-3-benzyloxycarbonylamino-1-chloroazetidin-2-one as an oil.

A stirring mixture of the oil and dried 4 Å molecular sieves in dry tetrahydrofuran (10 ml)was cooled to 0°–5° C. and trimethylphosphite (0.2 ml)was added after 15 minutes. After 30 minutes another portion (0.2 ml) of trimethylphosphitewas added and stirring was continued at 0°–5° C. for 45 minutes. The reaction was diluted with ethyl acetate, washed with water followed by saturated sodium bicarbonate solution, dried (sodium sulfate) and solvent was removed in vacuo giving an oil. Flash chromatography on silica gel (50 g) yielded the desired product (255 mg) as an oil upon elution with ethyl acetate. Crystallization from ethyl acetate-ether gave the desired product as a powder (154 mg).

EXAMPLE 2

[(S)-2-Oxo-3-[[(phenylmethoxy)carbonyl]amino]-1-azetidinyl]phosphonic acid, dipotassium salt (S)-[1-(Dimethoxyphosphinyl)-2-oxo-3-azetidinyl]-carbamic acid, phenylmethyl ester (63 mg; see example 1)was dissolved in dry dichloromethane (1 ml) and trimethylsilyl bromide (56 µl) was added. After stirring the mixture for 2½ hours at room temperature, ether was added followed by water (10 µl) causing a product to separate from solution as an oil. Solvent was removed invauo and the residue was dissolved in water by addition of 1.84 N potassium hydroxide solution (104 µl). Water was removed in vacuo and the residue was solidified with acetone-ether, triturated twice with ether and collected (64 mg). The product was chromatographed on HP20AG (HP20AG is macroporous styrene-divinylbenzene copolymer, Mitsubishi Chemical Industries) using a water-acetonitrile gradient elution. The dipotassium salt was eluted to give an oil (16 mg) after removal of the eluant in vacuo. The oil solidified with acetonitrileether, was triturated twice with ether, and collected yielding a powder.

Anal. Calc'd for $C_{11}H_{11}N_2O_6PK_2.H_2O$: C, 33.50; H, 3.58; N, 7.10; P, 7.85. Found: C, 33.73, 33.87; H, 3.41, 3.33; N, 7.23, 7.18; P, 8.03.

EXAMPLE 3

(S)-[2-Oxo-3-[(phenylacetyl)amino]-1-azetidinyl]phosphonic acid, dimethyl ester

3-[(Phenylacetyl)amino]-2-azetidinone (250 mg)was dissolved in a mixture of dry dimethylformamide (2 ml) and anhydrous tetrahydrofuran (5 ml). The mixture was cooled to −78° C., sec-butyllithium (0.83 ml of 1.4 N in cyclohexane) was added, stirring was continued for 8 minutes dimethylphosphorochloridate (187 µl) was added, and the mixture was stirred for 45 minutes at −78° C. After dilution with saturated aqueous sodium chloride and two extractions with ethyl acetate, the combined extracts were dried (sodium sulfate), filtered, and solvent was removed in vacuo yielding an oil. Thin-layer chromatography on plates developed in ethyl acetate gave the product as an oil which crystallized from ether. The solid was recrystallized from ethyl acetateether-pentane, triturated with ether, and dried in vacuo yielding 283 mg of the title compound as a powder, melting point 77.5°–81.5° C.

Anal. Calc'd for $C_{13}H_{17}N_2O_5P$(312.27): C, 50.00; H, 5.49; N, 8.97; P, 9.92. Found C, 50.12; H, 5.15; N, 9.02; P, 9.8.

EXAMPLE 4

(S)-[2-Oxo-3-[[(phenylmethoxy)carbonyl]amino]-1-azetidinyl]phosphonic acid, methyl ester, potassium salt (S)-[1-(Dimethoxyphosphinyl)-2-oxo-3-azetidinyl]-carbamic acid, phenylmethyl ester (100 mg; see example 1) was dissolved in 2 ml of acetonitrile, thiourea (23 mg) was added, and the mixture was refluxed under a nitrogen atmosphere for 20 hours. Solvent was then removed in vacuo and the residue was worked into a hygroscopic powder by triturating several times with anhydrous ether yielding (S)-[2-oxo-3-[[(phenylmethoxy)carbonyl]amino]-1-azetidinyl]phosphonic acid, methyl ester, thiuronium salt.

Dissolution of the salt in water and passage of the solution through a cation exchange resin (AGMP-50, K+ form), followed by removal of water in vacuo from the eluate gave the title potassium salt as an oil, which solidified upon addition of acetone-ether. After triturating twice with anhydrous ether, the product (66 mg), was obtained as a deliquescent powder, melting point 63°–67° C.

Anal Calc'd for $C_{12}H_{14}N_2O_6PK$ (352.33): C, 40.90 H, 4.00; N, 7.95; P, 8.79. Found: C, 40.69; H, 4.12; N, 8.00; P, 8.6.

EXAMPLE 5

(S)-[2-Oxo-3-[(phenylacetyl)amino]-1-azetidinyl]phosphonic acid, methyl ester, potassium salt Following the procedure of example 4, but substituting (S)-[2-oxo-3-[(phenylacetyl)amino]-1-azetidinyl]-phosphonic acid, dimethyl ester (see example 3) for (S)-[1-(dimethoxyphosphinyl)-2-oxo-3-azetidinyl]carbamic acid, phenylmethyl ester, yielded the title compound as a solid, melting point 242°–244° C.

Anal. Calc'd for $C_{12}H_{14}N_2O_5PK \cdot \frac{1}{2}H_2O$: C, 41.73; H, 4.38; N, 8.11; P, 8.97. Found: C, 41.62; H, 4.20; N, 8.18; P, 8.49.

EXAMPLE 6

[3S(Z)]-[3-[[(2-Amino-4-thiazolyl)(methoxyimino)acetyl]amino]-2-oxo-1-azetidinyl]phosphonic acid, methyl ester, potassium salt To pre-hydrogenated 10% palladium on charcoal (247.3 mg in 4 ml of 3:7 dimethylformamide:acetonitrile) was added a solution of (S)-[2-oxo-3-[[(phenylmethoxy)carbonyl]amino]-1-azetidinyl]phosphonic acid, methyl ester, potassium salt (494.5 mg; see example 4) in 10 ml of dimethylformamide:acetonitrile (3:7). The mixture was hydrogenated for 2 hours. The catalyst was removed by filtration through Celite. The filtrate was concentrated in vacuo without heating to remove acetonitrile and then diluted with 10 ml of dry dichloromethane. methane. This solution was added to a cold (0° C.) solution of (Z)-2-amino-α-(methoxyimino)4-thiazoleacetic acid (282.14 mg), N-hydroxybenzotriazole monohydrate (189.1 mg) and N,N-dicyclohexylcarbodiimide, 99% (289.6 mg, 1 eq.) in 3 ml of dimethylformamide (dry) under nitrogen. The mixture was stirred at 0° C. for one hour. The dicyclohexylurea was filtered. The filtrate had solvent removed in vacuo at 40° C. The residue was triturated with ethyl acetate to give 570 mg of the crude product which was purified by column chromatography on 100 ml of HP20AG, eluting with water; 103 mg of product was obtained.

EXAMPLE 7

[3S(Z)]-[3-[[(2-Amino-4-thiazolyl)(methoxyimino)acetyl]amino]-2-oxo-1-azetidinyl]phosphonic acid, methyl ester

[3S(Z)]-[3-[[(2-Amino-4-thiazolyl)(methoxyimino)acetyl]amino]-2-oxo-1-azetidinyl]phosphonic acid, methyl ester, potassium salt (103 mg; see example 6)was dissolved in 10 ml of distilled water and acidified to pH 2.4 with 0.3 N hydrochloric acid. The mixture was concentrated in vacuo to give a crude crop, which was dissolved in acetone and precipitated from water. The solid product was collected by filtration and dried overnight over phosphorous pentoxide in vacuo yielding 41 mg of product, melting point 117°-123° C.

Anal. Calc'd for $C_{10}H_{14}N_5PS$: C, 33.06; H, 3.88; N, 19.28; S, 8.83. Found: C, 16.62; H, 2.16; N, 9.05; S, 4.48; ash, 42.9.

(flame tests positive for potassium and chlorine)

EXAMPLE 8

[b

3S(Z)]-[3-[[(2-Amino-4-thiazolyl)(methoxyimino)acetyl]amino]-2-oxo-1-azetidinyl]phosphonic acid, dimethyl ester (S)-[1-(Dimethoxyphosphinyl)-2-oxo-3-azetidinyl]-carbamic acid, phenylmethyl ester (500 mg; see example 1) dissolved in 30 ml of absolute ethanol was added to pre-hydrogenated 10% palladium on charcoal (250 mg) in 30 ml of absolute ethanol. The mixture was hydrogenated for 35 minutes. The catalyst was removed by filtration through Celite. The filtrate was evaporated to dryness in vacuo without heating. The residue was dissolved in 7.5 ml of dry dichloromethane and added to a cold (0° C.) solution of (Z)-2-amino-α-(methoxyimino)-4-thiazoleacetic acid (306.5 mg) and N-hydroxybenzotriazole (205.8 mg) in 7.5 ml of dry dimethylformamide. To this mixture was added N,N-dicyclohexylcarbodiimide, 99% (295.5 mg) at 0° C. under nitrogen. The mixture was stirred at 0°-5° C. overnight under nitrogen. The dicyclohexylurea was filtered. The filtrate was stripped to dryness in vacuo. The residue was taken up in 45 ml of ethyl acetate and stirred at room temperature for 1 hour. The precipitate was collected by filtration. After drying, 259 mg of the crude product was obtained. The filtrate was washed with three 15 ml portions of 0.3 N hydrochloric acid, adjusted to pH=6.0 with sodium bicarbonate solution, and extracted with three 20 ml portions of ethyl acetate. The combined ethyl acetate extracts were dried over sodium sulfate, filtered and evaporated to give 70 mg of additional product. After crystallization from methanol-ethyl acetate, 108 mg of analytically pure product was obtained, melting point 191°-193° C.

Analysis: Calc'd for $C_{11}H_{16}N_5O_6SP$: C, 35.01; H, 4.27; N, 18.56; S, 8.50; P, 8.4. Found: C, 34.94; H, 4.31; N, 18.30; S, 8.24; P, 8.0.

EXAMPLE 9

(S)-[1-(Methoxymethylphosphinyl)-2-oxo-3-azetidinyl]-carbamic acid, phenylmethyl ester To a cold solution (−78° C.) of 3-benzyloxycarbonylamino-2-azetidinone (5.0 g) in 100 ml of dry tetrahydrofuran (freshly distilled over sodium) was added a solution of 1.4 M sec-butyllithium in cyclohexane (19.4 ml). After a few minutes the mixture was treated with methyl methylphosphorochloridate (2.7 ml) The mixture was stirred at −78° C. under nitrogen for 20 minutes. The resulting solution was poured into a mixture of 500 ml ethyl acetate and 250 ml of saturated sodium chloride. The organic layer was separated. The aqueous layer was extracted with two 250 ml portions of ethyl acetate. The combined ethyl acetate extracts were dried over sodium sulfate and filtered to remove the drying agent. The filtrate was evaporated to dryness to give 7.75 g of product. After flash chromatography on a silica gel column (750 g; 50 ml fractions eluted progressively with 600 ml amounts of ethyl acetate containing 10%, 20% and 30% of methanol), the desired product (3.55 g) was obtained in fractions 24–39.

EXAMPLE 10

(S)-[1-(Hydroxymethylphosphinyl)-2-oxo-3-azetidinyl]-carbamic acid, phenylmethyl ester, potassium salt A mixture of (S)-[1-(methoxymethylphosphinyl)-2-oxo-3-azetidinyl]carbamic acid, phenylmethyl ester (3.0 g; see example 9) and thiourea (3.68 g) in 48 ml of dry acetonitrile was heated under reflux for 18 hours. The resulting mixture was evaporated to dryness to give 6.68 g of crude product. After purification on a 200 ml column of ion-exchange resin (K+ form) (eluting with 30% acetone in water), 2.62 g of the desired product was obtained from fractions 3 and 4 (50 ml each fraction).

Recrystallization of 200 mg of product from methanol-acetonitrile yielded 135 mg of analytically pure material, melting point 164°-166° C.

Analysis for $C_{12}H_{14}N_2O_5PK \cdot H_2O$; Calc'd: C, 40.67; H, 4.55; N, 7.90; P, 8.74. Found: C, 40.76; H, 4.47; N, 8.00; P, 8.40.

EXAMPLE 11

(S)-[3-[[(2-Amino-4-thiazolyl)(methoxyimino)acetyl]amino]-2-oxo-1-azetidinyl]methylphosphinic acid, methyl ester (S)-[1-(Methoxymethylphosphinyl)-2-oxo-3-azetidinyl]carbamic acid, phenylmethyl ester, (339.1 mg; see example 9) was dissolved in 17 ml of 1:1 acetonitrile:absolute ethanol and added to pre-hydrogenated 10% palladium on charcoal catalyst, (169.6 mg) in 8.5 ml of absolute ethanol. The mixture was hydrogenated for 1 hour. The resulting mixture was filtered through Celite and the filtrate was concentrated to dryness. The residue was dissolved in 8.5 ml of dichloromethane, cooled in an ice bath and added to a cold (0° C.) mixture of (Z)-2-amino-α-(methoxyimino)-4-thiazoleacetic acid (210.6 mg) and N-hydroxybenzotriazole (141.5 mg) in 8.5 ml of dry dimethylformamide. To this mixture was added N,N-dicyclohexylcarbodiimide (216.4 mg) and the solution was stirred at 0°–5° C. overnight. Precipitated dicyclohexylurea was filtered off and the filtrate was evaporated to dryness in vacuo. The residue was taken up in 50 ml of ethanol, stirred at room temperature for ½ hour, and filtered to give 254.8 mg of crude product, which was triturated with acetonitrile yielding 58.2 mg of product, melting point 200°–202° C., dec.

Analysis Calc'd for $C_{11}H_{16}N_5O_5SP$: Calc'd: C, 36.55; H, 4.46; N, 19.38; S, 8.87; P, 8.57. Found: C, 38.58; H, 4.97; N, 18.65; S, 11.43; P, 6.7.

EXAMPLE 12

(S)-Methyl[2-oxo-3-[(phenylacetyl)amino]-1-azetidinyl]phosphinic acid, potassium salt (S)-[1-(Hydroxymethylphosphinyl)-2-oxo-3-azetidinyl]carbamic acid, phenylmethyl ester, potassium salt (500 mg; see example 10) was dissolved in 10 ml of water and added to prehydrogenated 10% palladium on charcoal catalyst (250 mg) in 10 ml of water; the mixture was hydrogenated for 1 hour. The resulting mixture was filtered through Celite. The filtrate was diluted with 20 ml of acetone, cooled to 0° C. and potassium bicarbonate (150 mg) was added (pH of solution is 7.9) followed by phenylacetyl chloride (250 μl) in 1 ml of acetone. The mixture was maintained at pH 6.7 with 10% potassium bicarbonate for 2 hours and then filtered. The filtrate was concentrated to give 934.3 mg of crude product, which was purified by medium pressure chromatography on 200 ml of HP20AG resin. The product was eluted with 5% acetonitrile in water yielding 49.3 mg of a deliquescent powder. After trituration with ether-acetonitrile and lyophilization 42 mg of product as a powder was obtained, melting point 187°–190° C.

Analysis Calc'd for $C_{12}H_{14}N_2O_4PK$: Calc'd: C, 44.99; H, 4.40; N, 8.75; P, 9.67. Found: C, 44.18; H, 4.85; N, 6.42; P, 7.6.

EXAMPLE 13

(S)-[1-(Ethoxyphenylphosphinyl)-2-oxo-3-azetidinyl]carbamic acid, phenylmethyl ester To a solution of 3-benzyloxycarbonylamino-2-azetidinone (5.0 g) in dry tetrahydrofuran (125 ml), cooled to −78° C., was added sec-butyl lithium (18.5 ml) and the mixture was stirred for 5 minutes. Ethyl chlorophenylphosphonate (4.71 g) was added and the mixture was stirred for 1 hour at −78° C. followed by the addition of 125 ml of saturated sodium chloride solution. The mixture was then extracted twice with 125 ml portions of ethyl acetate and the extracts were combined, dried over anhydrous sodium sulfate and the solvent removed in vacuo yielding the crude product as a foam. The crude product was purified by chromatography on silica gel (750 g), eluting with dichloromethane:ethyl acetate (1:1) followed by ethyl acetate. The ethyl acetate fractions were stripped and the residue triturated with ether to yield 4.94 g of product.

Anal. Calc'd for $C_{19}H_{21}N_2O_5P$ (388.36): C, 58.76 H, 5.45; N, 7.21; P, 7.98. Found: C, 58.74; H, 5.42; N, 7.31; P, 7.73.

EXAMPLE 14

(S)-[1-(Hydroxyphenylphosphinyl)-2-oxo-3-azetidinyl]carbamic acid, phenylmethyl ester, potassium salt A mixture of 1.22 g of (S)-[1-(ethoxyphenylphosphinyl)-2-oxo-3-azetidinyl]carbamic acid, phenylmethyl ester (see example 13) and 1.28 g of bis-trimethylsilylacetamide in dry dichloromethane (15 ml) was allowed to stir under nitrogen for 15 minutes to remove any water that may be present. Trimethylsilyl bromide (0.721 g) was added and the mixture was stirred at room temperature for 20 hours. The mixture was poured into 40 ml of 0.5 M pH 5.5 monobasic potassium phosphate buffer; the pH was adjusted to 6.5 with 1.85 N potassium hydroxide. The aqueous layer was separated and the organic layer was extracted with water. The aqueous extracts were combined and the water was removed in vacuo. The residue was purified by column chromatography on 150 ml of HP20AG, eluting with water (1400 ml) followed by 20% acetonitrile/water. Removal of the solvent in vacuo yielded a solid which was triturated with acetone and then ether to obtain the product as a crystalline solid (674 mg; melting point 174°–177° C., dec.).

Anal. Calc'd for $C_{17}H_{16}N_2O_5PK$ (398.40): C, 51.25; H, 4.05; N, 7.03; P, 7.78. Found: C, 50.81; H, 4.07; N, 6.97; P, 7.70.

EXAMPLE 15

[3S(Z)]-[3-[[(2-Amino-4-thiazolyl)(methoxyimino)acetyl]amino]-2-oxo-1-azetidinyl]methylphosphinic acid, potassium salt To a suspension of pre-hydrogenated 10% palladium on charcoal (280 mg) in methanol (11 ml) was added a solution of (S)-[1-(hydroxymethylphosphinyl)-2-oxo-3-azetidinyl]carbamic acid, phenylmethyl ester, potassium salt (560 mg, see example 10) in methanol (11 ml). The mixture was stirred for ½ hour under an atmosphere of hydrogen, filtered through Celite, and the filter bed was washed with methanol. The filtrate and washings were concentrated in vacuo. The hydrogenation was repeated twice more with fresh catalyst yielding (S)-(3-amino-2-oxo-1-azetidinyl)methylphosphinic acid, potassium salt containing about 10% of the starting azetidinone.

To a solution of (S)-(3-amino-2-oxo-1-azetidinyl)methylphosphinic acid, potassium salt in dimethylformamide (22 ml) at 0°–5° C. was added (Z)-2-amino-α-(methoxyimino)-4-thiazoleacetic acid (286 mg), N-hydroxybenzotriazole hydrate (192 mg), and dicyclohexylcarboiimide (292 mg). The mixture was stirred overnight at 5° C., filtered, and solvent was removed in vacuo. Trituration of the residue with ethyl acetate gave a solid (431 mg), which was chromatographed on HP20AG resin (150 ml). The product was eluted with water, then solidified and triturated with acetone to give (136 mg) of the title compound.

Anal. Calc'd for $C_{10}H_{13}N_5O_5SPK\cdot\frac{1}{2}H_2O$: C, 30.37; H, 3.57; N, 17.71; S, 8.11; P, 7.84. Found: C, 30.59; H, 3.93; N, 17.55; S, 8.21; P, 7.6.

EXAMPLE 16

[3S(Z)]-[3-[[(2-Amino-4-thiazolyl)(methoxyimino)acetyl]amino]-1-azetidinyl]phosphonic acid, methyl ester, potassium salt A solution of 1 g of (S-[2-oxo-3-[[(phenylmethoxy)carbonyl]amino]-1-azetidinyl]phosphonic acid, methyl ester, potassium salt (see example 4) in ethanol (30 ml) was added to a pre-hydrogenated suspension of 10% palladium on charcoal (0.5 g) in ethanol (10 ml). The mixture was stirred for 2½ hours under a stream of hydrogen. After filtration through Celite on a Millipore filter, ethanol was removed in vacuo giving a foam. A solution of this foam in dimethylformamide (15 ml) was added to a mixture of (Z)-2-amino-α-(methoxyimino)-4-thiazoleacetic acid (598 mg), N-hydroxybenzotriazole hydrate (401 mg) and dicyclohexylcarbodiimide (613 mg) in dry dimethylformamide (5 ml), which had been stirred for 10 minutes at room temperature.

The entire reaction mixture was stirred for 17 hours at room temperature, filtered, and solvent was removed from the filtrate in vacuo giving an oil. Solidification and trituration of the oil with ethyl acetate yielded a solid, which was dissolved in water. The solution was filtered to remove suspended dicyclohexylurea, the pH of the filtrate was raised to 6.6 with dilute potassium bicarbonate, and the concentrated solution was chromatographed on HP20 resin (200 ml). The product was eluted with water, crystallized twice from a mixture of methanol:acetone (1:2), washed with acetone, and dried to give (151 mg) of product as a solid.

Anal. Calc'd for $C_{10}H_{13}N_5O_6SPK\cdot\frac{1}{2}H_2O$: C, 29.41; H, 3.45; N, 17.11; S, 7.83; P, 7.57. Found: C, 29.51, 29.39; H, 3.79, 3.49; N, 16.75, 16.75; S, 7.83; P, 7.40.

EXAMPLE 17

(S)-[2-Oxo-3-[(phenylacetyl)amino]-1-azetidinyl]-phenylphosphinic acid, potassium salt To a pre-hydrogenated 10% palladium on charcoal (300 mg in 30 ml of methanol) catalyst was added a solution of (S)-[1-(hydroxyphenylphosphinyl)-2-oxo-3-azetidinyl]carbamic acid, phenylmethyl ester (876 mg; see example 14) in 20 ml of methanol. The mixture was hydrogenated for 2 hours. The catalyst was removed by filtration through Celite. The filtrate was concentrated in vacuo, without heating, yielding 580 mg of (S)-[(2-oxo-3-amino)-1-azetidinyl]phenylphosphinic acid, potassium salt.

To a mixture of the 3-aminoazetidinylphenylphosphinic acid (580 mg) and potassium bicarbonate (374 mg) in acetone (18 ml) and water (12 ml) was added phenylacetyl chloride (374 mg). The mixture was allowed to stir for 24 hours at 5° C. The solvent was removed in vacuo yielding a solid. The crude residue was chromatographed on 175 ml HP20AG resin, eluting with water (400 ml) followed by eluting with a solvent gradient of 500 ml each of 60% acetonitrile/water and water. Removal of solvent in vacuo yielded a solid which was triturated with acetone and ether to yield 250 mg of product, melting point 176°–178° C., dec.

Anal. Calc'd for $C_{17}H_{16}N_2O_4PK$ (382.40): C, 53.39; H, 4.22; N, 7.33; P, 8.10. Found: C, 53.08; H, 4.22; N, 7.30; P, 8.1.

EXAMPLE 18

[3S(Z)]-[3-[[(2-Amino-4-thiazolyl)(methoxyimino)acetyl]amino]-2-oxo-1-azetidinyl]phenylphosphinic acid, potassium salt (S)-[(2-Oxo-3-amino)-1-azetidinyl]phenylphosphinic acid, potassium salt (330 mg; see example 17) was added to a cold (0° C.) solution of (Z)-2-amino-α-(methoxyimino)-4-thiazoleacetic acid (254 mg), N-hydroxybenzotriazole hydrate (193 mg) and N,N-dicyclohexylcarbodiimide, 99% (260 mg) in 4 ml of dry dimethylformamide under nitrogen. The mixture was stirred at 5° C. for 18 hours. The dicyclohexylurea was filtered and dimethylformamide was removed in vacuo at 40° C. The pH of the aqueous solution of the residue was adjusted to pH 6.5 and the crude product was purified by column chromatography on 150 ml of HP20AG, eluting with water (850 ml) followed by 10% acetonitrile in water (650 ml). Removal of solvent under reduced pressure yields a solid, which was triturated with acetone and then ether to yield 410 mg of the title compound, melting point 183°–185° C., dec.

Anal. Calc'd for $C_{15}H_{15}N_5O_5PS\cdot K$ (447.46): C, 40.26, H, 3.38; H, 15.65; S, 7.17; P, 6.92. Found: C, 40.18; H, 3.56; N, 15.34; S, 7.20; P, 6.90.

EXAMPLE 19

[3S(Z)]-2-[[[1-(2-Amino-4-thiazolyl)-2-[[1-(hydroxymethoxyphosphinyl)-2-oxo-3-azetidinyl]amino]-2-oxoethylidene]amino]oxy]-2-methylpropanoic acid benzhydryl ester 3-Benzyloxycarbonylamino-2-oxo-1-azetidinylphosphonic acid, methyl ester, potassium salt (250 mg; see example 4) in ethanol (7 ml) was added to a pre-hydrogenated suspension of 10% palladium on charcoal (125 mg) in ethanol (3 ml). The mixture was vigorously stirred under a hydrogen atmosphere for 0.5 hour, the atmosphere was exchanged for fresh hydrogen, and stirring was continued for an additional 0.5 hour. The catalyst was then replaced and the mixture was stirred for another 15 minutes under hydrogen, filtered through Celite on a Millipore filter and solvent was removed in vacuo giving (S)-3-amino-2-oxo-1-azetidinylphosphonic acid, methyl ester, potassium salt.

An active ester was formed by stirring (Z)-2-amino-α-[[2-(diphenylmethoxy)-1,1-dimethyl-2-oxoethoxy]imino]4-thiazoleacetic acid, (327 mg) N-hydroxybenzotraiazole hydrate (108 mg) and dicyclohexylcarbodiimide (146 mg) in dimethylformamide (3 ml) for 1½ hours at room temperature. (S)-3-Amino-2-oxo-1-azetidinylphosphonic acid methyl ester, potassium salt in dimethylformamide (3 ml) was added and the mixture was stirred at room temperature overnight. Solvent was removed in vacuo, the residue was taken up in water, the pH was adjusted to 6.5 with dilute potassium hydroxide, and the mixture was filtered to remove dicyclohexylurea. The pH of the filtrate was lowered to 2.5 with dilute hydrochloric acid causing a precipitate to form. The wet solid was collected by filtration, the filter cake was triturated with dry ether causing a gum to form, which was re-solidified with acetone yielding the product as a tan powder (205 mg).

The above aqueous filtrate was lyophilized and triturated with acetone yielding more product as a colorless solid (57 mg). A sample of this material was crystallized from methanol:acetone, melting point 159.5°–168° C., dec.

Anal. Calc'd for $C_{26}H_{28}N_5O_8PS \cdot \frac{1}{2}H_2O$) (610.58). C, 51.14; H, 4.79; N, 11.47; P, 5.07; S, 5.25. Found: C, 50.79; H, 4.74; N, 11.21; P, 5.1; S, 5.05.

EXAMPLE 20

[3S(Z)]-2-[[[1-(2-Amino-4-thiazolyl)-2-[[1-(hydroxymethoxyphosphinyl]-2-oxo-3-azetidinyl]amino]-2-oxoethylidene]amino]oxy]-2-methylpropanoic acid, dipotassium salt

[3S(Z)]-2-[[[1-(2-Amino-4-thiazolyl)-2-[[1-(hydroxymethoxyphosphinyl]-2-oxo-3-azetidinyl]amino]-2-oxoethylidene]amino]oxy]-2-methylpropanoic acid benzhydryl ester, (200 mg) (see example 19) was suspended in anisole (1.5 ml), cooled in an ice-methanol bath at $-24°$ C., and trifluoroacetic acid (3 ml) was added. The mixture was stirred at $-24°$ to $-12°$ C. for 1.25 hours, diluted with dry toluene (10 ml) and solvent was removed in vacuo at or below 19° C. The residual oil was solidified and triturated several times with ether giving a powder. After dissolving the powder in water, the pH was adjusted to 6.1 using dilute potassium hydroxide and hydrochloric acid. The solution was purified on an HP20AG column (25 ml); water was removed in vacuo, and the desired product was obtained as a powder (107 mg) after trituration with acetone.

Anal. Calc'd for $C_{13}H_{16}N_5O_8PSK_2$(511.55): C, 30.52; H, 3.15; N, 13.69. Found: C, 28.03; H, 2.99; N, 10.16; Cl, 2.73.

Analysis for chlorine indicates that sample contains about 5% potassium chloride.

EXAMPLE 21 d,Z-(cis)-3-Benzyloxycarbonylamino-4-methoxycarbonylazetidin-2-one-1-phosphonic acid, dimethyl ester (cis)-3-Benzyloxycarbonylamino-4-methoxycarbonylazetidin-2-one (100 mg) was dissolved in dry tetrahydrofuran (2 ml), cooled to $-78°$ C. and treated with a 1.35 M solution of sec-butyllithium (0.27 ml) in cyclohexane. After stirring several minutes, dimethylphosphorochloridate (37 ml) was added and the mixture was stirred for 1.5 hours at $-78°$ C. A crude oil was obtained by pouring the mixture into saturated sodium chloride solution, extracting twice with ethyl acetate, drying the combined extracts (sodium sulfate) and removing solvent in vacuo. Purification on preparative thin-layer silica gel plates yielded the product as an oil (80 mg).

EXAMPLE 22

(S)-1-(Methoxy(1-piperidyl)phosphinyl)-2-oxo-3-azetidinyl]carbamic acid, phenylmethyl ester To a solution of (S)-3-benzyloxycarbonylaminoazetidin-2-one (250 mg) in dry tetrahydrofuran (7 ml) cooled to $-78°$ C. was added a 1.35 M solution of sec-butyl lithium in cyclohexane (0.85 ml). After stirring at $-78°$ C. for 0.5 hour, the mixture was added to a solution of methyl dichlorophosphate (115 μl) in tetrahydrofuran (3 ml) cooled to $-78°$ C. The reaction was stirred for 1 hour at $-78°$ C., dry piperidine (227 μl) is added, and the solution was allowed to warm to room temperature while stirring for 1.5 hours. Saturated sodium chloride solution (20 ml) was added and the resulting mixture was extracted with two 25 ml portions of ethyl acetate. The combined extracts were dried (sodium sulfate) and removal of solvent in vacuo yields an oil, which was purified on silica gel plates developed in 9:1 ethyl acetate:methanol. The desired product was obtained as an oily mixture of diastereomers.

EXAMPLE 23

(S)-3-[[(2-Amino-4-thiazolyl)(methoxyimino)acetyl]amino]-2-oxo-1-azetidinephosphonic acid A mixture of [3S(Z)]-[3-[[(2-amino-4-thiazolyl)(methoxyimino)acetyl]amino]-2-oxo-1-azetidinyl]phosphonic acid, dimethyl ester (148 mg; see example 8) and bis-trimethylsilylacetamide (256 mg) in dry dichloromethane (6 ml) and dry dimethylformamide (0.8 ml) was allowed to stir under nitrogen for 15 minutes. Trimethylsilyl bromide (192 mg) was added at 5° C. and the reaction followed by thin-layer chromatography for 6 hours; noting that starting material was still present, additional amounts of bis-trimethylsilylacetamide (256 mg) and trimethylsilyl bromide (192 mg) were added. The reaction was then allowed to stir overnight at 5° C. under nitrogen. The solvents were removed in vacuo; redissolving the residue in dry toluene (three 20 ml portions) several times and then removing the toluene in vacuo aids in the removal of any residual trimethylsilyl bromide. The residue was next taken up in dry tetrahydrofuran (15 ml) and filtered to remove the insoluble material. The tetrahydrofuran solution containing the product, when treated with 2 equivalents of distilled aniline (76 μl) in ethanol (3 ml), precipitated 144 mg of a solid. The proton NMR spectrum showed that a mono anilinium salt was formed. The anilinium salt (128 mg) was placed on a 20 ml HP20AG column and eluted with 200 ml of water. The product was isolated in fractions 5, 6, and 7 (8 ml fractions are collected) and these were combined and lyophilized to yield 18 mg of the product as a zwitterion, melting point 182° C., dec.

Anal. Calc'd for $C_9H_{12}N_5SPO_6$ (MW 349.28) C, 30.95; H, 3.46; N, 20.05. Found: C, 33.97; H, 4.04; N, 19.84.

EXAMPLE 24

[3S(Z)]-[3-[[(2-Amino-5-chloro-4-thiazolyl)(methoxyimino)acetyl]amino]-1-azetidinyl]phosphonic acid, methyl ester, potassium salt (A) (S)-(3-Amino-2-oxo-1-azetidinyl)phosphonic acid, methyl ester, potassium salt (S)-[2-Oxo-3-[[(phenylmethoxy)carbonyl]amino]-1-azetidinyl]phosphonic acid, methyl ester, potassium salt (150 mg; see example 4) in ethanol was hydrogenated over 10% palladium on charcoal (75 mg) at 1 atmosphere. Catalyst was removed by filtration through Celite on a Millipore filter, and the solvent was removed in vacuo yielding the title compound.

(B)

[3S(Z)]-[3-[[(2-Amino-5-chloro-4-thiazolyl)(methoxyimino)acetyl]amino]-1-azetidinyl]phosphonic acid, methyl ester, potassium salt (Z)-2-Amino-5-chloro-α-(methoxyimino)-4-thiazoleacetic acid (100 mg) dissolved in 2 ml of dimethylformamide was treated with N-hydroxybenzotriazole (69 mg) and dicyclohexylcarbodiimide (93 mg). A solution of (S)-(3-amino-2-oxo-1-azetidinyl)phosphonic acid, methyl ester, potassium salt in 2.5 ml of dimethylformamide was added and the mixture was stirred for 2 days at room temperature. Precipitated dicyclohexylurea was removed by filtration and solvent was removed in vacuo. The residual oil was taken up in water, the pH was adjusted to 6.6 with dilute sodium bicarbonate solution, and the solution was filtered and concentrated in vacuo. Chromatography on Diaion HP20 resin (25 ml), eluting with water, gave the desired product as a glass. Trituration with acetonitrile-ether, followed by ether, gave 52 mg of the title compound.

Anal. calc'd for $C_{10}H_{12}ClN_5O_6PSK \cdot 0.5$ dimethylformamide: C, 29.23; H, 3.31; N, 16.31. Found: C, 29.21; H, 3.51; N, 15.65.

EXAMPLE 25

[3S(R)]-[3-[[[[[4-Ethyl-2,3-dioxo-1-piperazinyl)carbonyl]amino]phenyl]acetyl]amino]-2-oxo-1-azetidinyl]-phosphonic acid, methyl ester, potassium salt An active ester was formed by stirring (R)-α-[[(4-ethyl-2,3-dioxo-1-piperazinyl)carbonyl]amino]benzeneacetic acid (591 mg), N-hydroxybenzotriazole hydrate (284 mg) and dicyclohexylcarbodiimide (382 mg) in 6 ml of dimethylformamide for 1 hour at 0° C. (S)-(3-Amino2-oxo-1-azetidinyl)phosphonic acid, methyl ester, potassium salt (400 mg, see example 24A) in 1 ml of dimethylformamide was added and the mixture was stirred at room temperature overnight. Solvent was removed in vacuo, the residue was taken up in 4 ml of water and the precipitated dicyclohexylurea was removed by filtration. The pH of the mixture was adjusted to pH 6.8 by the addition of potassium bicarbonate solution. The solution was applied to a 125 ml column of HP20 resin and sequential elution with water, 10% acetone in water and finally 20% acetone in water provided 120 mg of the title compound.

Anal. Calc'd for $C_{19}H_{23}N_5O_8PK$: C, 42.45; H, 4.69; N, 13.03; P, 5.76. Found: C, 42.42; H, 4.46; N, 12.84; P, 5.8.

EXAMPLE 26

[3S(R)]-[3-[(Aminophenylacetyl)amino]-2-oxo-1-azetidinyl]phosphonic acid, methyl ester (A)

[3S(R)]-[3-[[[[[(4-Methoxybenzyl)oxy]carbonyl]amino]phenylacetyl]amino]-2-oxo-1-azetidinyl]phosphonic acid, methyl ester A solution of 1-hydroxybenzotriazole hydrate (536 mg) and p-methoxybenzyl phenylglycine (116 mg) in 10 ml of dry dimethylformamide was cooled to 0° C. and treated with dicyclohexylcarbodiimide (722 mg). This mixture was stirred at 0° C. for 30 minutes. At this time (S)-(3-amino-2-oxo-1-azetidinyl)phosphonic acid, methyl ester, potassium salt (655 mg; see example 24A) was added to the reaction mixture and the pH maintained between pH 6.5 and pH 7.0 by adding triethylamine as necessary. The reaction was stirred at 0° C. for 30 minutes, and then at ambient temperature for 18 hours. The dimethylformamide was evaporated in vacuo at 30° C., and the residue was slurried in acetone to precipitate dicyclohexylurea. The solid was removed and washed with three 5 ml portions of acetone. The acetone solutions were combined and concentrated in vacuo yielding an oily residue. The oil was dissolved in 6 ml of water and applied to a column of 75 ml of Dowex 50X2-400 (K⊕) resin; elution with water yielded 924 mg of impure potassium salt. A 900 mg portion of this material was applied to a 100 ml column of HP-20 resin in water. Elution with water followed by lyophilization of the appropriate fractions yielded 517 mg of the title compound, melting point 140°-144° C., dec.

(B)

[3S(R)]-[3-[(Aminophenylacetyl)amino]-2-oxo-1-azetidinyl]phosphinic acid, methyl ester

[3S(R)]-[3-[[[[[(4-Methoxybenzyl)oxy]carbonyl]amino]phenylacetyl]amino]-2-oxo-1-azetidinyl]phosphonic acid, methyl ester (378 mg) was suspended in dry anisole (12 ml) and cooled to 0° C. in an ice bath under nitrogen. Distilled trifluoroacetic acid (20 ml) was added and stirring at 0° C. was continued for 3 hours. The reaction was diluted with 30 ml of dry toluene and the solvents removed in vacuo, yielding a semisolid. Toluene (25 ml) was added and once more removed in vacuo yielding a solid (304 mg). The solid was dissolved in 5 ml of water and the pH of the mixture raised to pH 4 by adding 5% potassium bicarbonate solution. The solution was then applied to a 125 ml column of HP-20 resin in water. Elution with water followed by lyophilization yielded 168 mg of the title compound as a solid.

Anal. Calc'd. for: $C_{12}H_{16}N_3O_5P \cdot 1.3$ Mole $H_2O$ C, 42.82; H, 5.57; N, 12.48; P, 9.2.

found: C, 42.82; H, 5.39; N, 12.45; P, 9.1.

EXAMPLE 27

(S)-[1-(Diethoxyphosphinyl)-2-oxo-3-azetidinyl]carbamic acid, phenylmethyl ester To a solution of (S)-3-benzyloxycarbonylamino-2-azetidinone (1.0 g) in dry tetrahydrofuran (30 ml) cooled to −78° C. was added a solution of n-butyl lithium (2.91 ml of 1.56 M in hexane). After stirring several minutes diethyl phosphorochloridate (0.66 ml) 4.54 mmol) was added and the mixture was stirred at −78° C. for 1.5 hours. Saturated aqueous sodium chloride solution was added and after extracting three times with ethyl acetate, the combined extracts were dried ($Na_2SO_4$), and solvent was removed in vacuo. The resulting foam was chromatographed on a silica gel column (50 g, 60–200 mesh) collecting ca. 25 ml fractions.

| Fractions | Eluant |
| --- | --- |
| 1–10 | $CH_2Cl_2$ |
| 11–20 | 25% EtOAc-75% $CH_2Cl_2$ |
| 21–29 | 50% EtOAc-50% $CH_2Cl_2$ |
| 30–40 | EtOAc |

The desired product (1.28 g) was obtained as an oil from fractions 23–37.

EXAMPLE 28

(S)-[2-Oxo-3-[[(phenylmethoxy)carbonyl]amino]-1-azetidinyl]phosphonic acid, ethyl ester, potassium salt A mixture of (S)-[1-(diethoxyphosphinyl)-2-oxo-3-azetidinyl]carbamic acid, phenylmethyl ester (807 mg; see example 27) and thiourea (782 mg) in acetonitrile (18 ml) was refluxed under a nitrogen atmosphere for 48 hours. The mixture was concentrated in vacuo, diluted with acetonitrile (5 ml), and refluxed for ca. 3 hours more. Solvent was removed in vacuo, the residue was dissolved in water, tetrabutylammonium hydrogen sulfate (2.05 mmol) was added, the ion-paired product was extracted six times at pH 7 with dichloromethane and dried ($Na_2SO_4$). Removal of solvent gave an oil which was dissolved in water with enough acetone to make the mixture homogeneous. The solution was chromatographed on an ion-exchange column (Dowex 50X2-400 resin, K⊕ from, 30 ml) eluting with water (25 ml fractions). The first fraction gave pure product obtained as a powder (90 mg) after trituration with ethyl acetate-ether and then ether. Subsequent fractions were purified on HP-20 resin (50 ml) to yield more product (406 mg).

Anal. Calc'd for $C_{13}H_{16}N_2O_6PK.1.77H_2O$: C, 39.20; H, 4.94; N, 7.04; P, 7.77. Found: C, 39.20; H, 4.78; N, 7.24; P, 7.40.

EXAMPLE 29

[3S(Z)]-2-[[[1-(2-Amino-4-thiazolyl)-2-[[1-(ethoxyhydroxyphosphinyl)-2-oxo-3-azetidinyl]amino]-2-oxoethylidene]amino]oxy]-2-methylpropanoic acid, dipotassium salt (A)
[3S(Z)]-2-[[[1-(2-Amino-4-thiazolyl-2-[[1-(ethoxyhydroxyphosphinyl)-2-oxo-3-azetidinyl]amino]-2-oxoethylidene]amino]oxy]-2-methylpropanoic acid, benzhydryl ester To a pre-hydrogenated suspension of 10% palladium on charcoal (150 mg) in ethanol was added a solution of (S)-[2-oxo-3-[[(phenylmethoxy)carbonyl]amino]-1-azetidinyl]phosphonic acid, ethyl ester, potassium salt (300 mg; see example 28) in ethanol. After 1.5 hours hydrogenolysis was complete, catalyst was removed by filtration through Celite on a Millipore filter, and solvent was removed from the filtrate in vacuo without heating. Coupling was performed with a mixed anhydride generated from (Z)-2-amino-α-[[2-(diphenylmethoxy)-1,1-dimethyl-2-oxoethoxy]imino]-4-thiazoleacetic acid (417 mg) dissolved in dry tetrahydrofuran (5 ml) and cooled in an ice-methanol bath at −15° to −20° C. and then treated with diphenyl phosphorochloridate (186 μl) followed by triethylamine (125 μl). After stirring the mixture for 45 minutes at low temperature, it was added to a solution of the hydrogenolysis product in water and vigorously stirred. The pH was adjusted to ca. 6–7 with dilute potassium bicarbonate solution while stirring cold for 4.5 hours. Then solvent was removed in vacuo, the residue was re-dissolved in water and the pH was lowered to 1.5 with dilute hydrochloric acid. After collecting the solid by filtration and triturating with water, the title compound was obtained (625 mg).

(B)
[3S(Z)]-2-[[[1-(2-Amino-4-thiazolyl-2-[[1-(ethoxyhydroxyphosphinyl)-2-oxo-3-azetidinyl]amino]-2-oxoethylidene]amino]oxy]-2-methylpropanoic acid, dipotassium salt

[3S(Z)]-2-[[[1-(2-Amino-4-thiazolyl-2-[[1-(ethoxyhydroxyphosphinyl)-2-oxo-3-azetidinyl]amino]-2-oxoethylidene]amino]oxy]-2-methylpropanoic acid, benzhydryl ester (601 mg) was suspended in dry anisole (3 ml), cooled to 0°–5° C., trifluoroacetic acid (6 ml) was added and the mixture was stirred for 2.5 hours. Dilution with dry benzene (11 ml) and concentration under reduced pressure gave an anisole-containing oil which was worked into a hygroscopic powder with ether-pentane and then washed with ether. The solid was dissolved in water, the pH was raised to pH 6.8 with dilute potassium bicarbonate solution, and the resulting solution was chromatographed on an HP-20 column (60 ml). The product was rapidly eluted with water, concentrated to a residue and triturated once with acetonitrile and twice with ether to give 277 mg of the title compound as a solid, melting point 200° C.

Anal. calc'd for $C_{14}H_{18}N_5O_8PSK_2.1.77\ H_2O$: C, 30.20; H, 3.88; N, 12.58; S, 5.76; P, 5.56. Found: C, 30.20; H, 3.65; N, 12.60; S, 5.65; P, 5.5.

EXAMPLE 30

[3S(Z)]-[3-[[(2-Amino-4-thiazolyl)(methoxyimino)acetyl]amino]-2-oxo-1-azetidinyl]phosphonic acid, ethyl ester To a solution of (Z)-2-amino-α-(methoxyimino)-4-thiazoleacetic acid (30 mg) in 1 ml of dimethylformamide was added N-hydroxybenzotriazole hydrate (23 mg) and dicyclohexylcarbodiimide (31 mg). After stirring the mixture for about 4 minutes at room temperature, a solution of (S)-(3 amino-2-oxo-1-azetidinyl)phosphonic acid, ethyl ester, potassium salt generated from (S)-[2-oxo-3-[[(phenylmethoxy)carbonyl]amino]-1-azetidinyl]phosphonic acid, ethyl ester, potassium salt (60 mg; see example 28) using the hydrogenolysis procedure described in example 29A, was added in 1.7 ml of dimethylformamide; stirring was continued for 24 hours under a nitrogen atmosphere. Solvent was removed in vacuo, and the residue was dissolved in water, filtered, the pH of the filtrate was raised to 5.6 with dilute potassium hydroxide and the mixture was chromatographed on HP-20 resin (8 ml). The product was triturated with acetone, ether, acetonitrile, and again with ether, and dried to give 57 mg of a powder. The powder was dissolved in water, the pH was lowered to 2.5 with dilute hydrochloric acid, and chromatography on about 10 ml of HP-20 resin eluting with water gave the title compound, which crystallized from acetone-ether (yield: 39 mg).

EXAMPLE 31

[3S(Z)]-[3-[[(2-Amino-4-thiazolyl)(methoxyimino)acetyl]amino]-2-oxo-1-azetidinyl]phosphonic acid, 2-fluoroethyl ester, potassium salt (A)
(S)-[3-[[(1,1-Dimethylethoxy)carbonyl]amino]-2-oxo-1-azetidinyl]phosphonic acid, 2-fluoroethyl ester, potassium salt To phosphoryl chloride (50 ml) in 40 ml of carbon tetrachloride at ambient temperature was added dropwise 2-fluoroethanol (25 g). The reaction was stirred overnight at room temperature and then refluxed for 3 hours. Vacuum distillation at 88°–98° C. yielded 21.0 g of 2-fluoroethyl dichlorophosphate.

A solution of (S)-3-[[(1,1-dimethylethoxy)carbonyl]amino]azetidin-2-one in 20 ml of dry tetrahydrofuran at −78° C. was treated with 1.94 ml of 1.7 N n-butyl lithium. After 30 minutes the reaction mixture was added to 2-fluoroethyl dichlorophosphate (0.39 ml) in 10 ml of tetrahydrofuran at −75° C. and stirred for 1 hour. The resulting mixture was then poured into a rapidly stirring suspension of 30 ml of pH 6 phosphate buffer and 30 ml of dioxane at 0° C. The reaction mixture was stirred at ambient temperature for 1 hour and then placed at 5° C. overnight. Evaporation of the volatiles followed by chromatography on HP-20 (eluting with water, 20% acetone-water, and 40% acetone-water) yielded 420 mg of the title compound.

(B)
[3S(Z)]-[3-[[(2-Amino-4-thiazolyl)(methoxyimino)acetyl]amino]-2-oxo-1-azetidinyl]phosphonic acid, 2-fluoroethyl ester, potassium salt Diisopropylethylamine (0.115 ml) was added to 121 mg of (Z)-2-amino-α-(methoxyimino)4-thiazoleacetic acid (121 mg) in 2 ml of dimethylformamide at 23° C. The mixture was cooled to −20° C., diphenylphosphinyl chloride (0.110 ml) was added, and the resulting mixture was stirred for 2 hours to give a mixed anhydride.

(S)-[3-[[(1,1-Dimethylethoxy)carbonyl]amino]-2-oxo-1-azetidinyl]phosphonic acid, 2-fluoroethyl ester, potassium salt (210 mg) was dissolved in 0.3 ml of anisole and cooled to 0° C. Trifluoroacetic acid (3 ml) was added, and the resulting mixture was stirred at 0° C. for 1 hour. The volatiles were evaporated and the residue was triturated with petroleum ether and anhydrous ether to yield the trifluoroacetic acid salt of (S)-(3-amino-2-oxo-1-azetidinyl)phosphonic acid, 2-fluoroethyl ester as a powder. After evacuation for 1 hour, the residue was dissolved in 2 ml of dimethylformamide, and upon cooling to 0° C., 0.5 ml of diisopropylethylamine was added. The reaction mixture containing the mixed anhydride was then added to the azetidinone.

After stirring at 5° C. overnight, the volatiles were removed under vacuum. The residue was purified by column chromatography with water on Dowex 50X2-400 resin (K⊕ form) followed by chromatography on HP-20 (eluting with water) to yield 146 mg of the title compound, melting point 170°–215° C., dec.

Anal. Calc'd for $C_{11}H_{14}FN_5O_6PS.K.2H_2O$: C, 28.14; H, 3.83; N, 14.92. Found: C, 28.18; H, 3.63; N, 14.80.

EXAMPLE 32

(3S(Z))-[3-[[(2-Amino-4-thiazolyl)(methoxyimino)acetyl]amino]-2-oxo-1-azetidinyl]phosphonic acid, 2,2,2-trifluoroethyl ester, potassium salt (A)
(S)-[3-[[(1,1-Dimethylethoxy)carbonyl]amino]-2-oxo-1-azetidinyl]phosphonic acid, 2,2,2-trifluoroethyl ester, potassium salt A solution of (S)-3-[[(1,1-dimethylethoxy)carbonyl]amino]azetidin-2-one (557 mg) in 20 ml of dry tetrahydrofuran at −78° C. was treated with 1.94 ml of 1.7 N n-butyl lithium. After 30 minutes the reaction mixture was added to 2,2,2-trifluoroethyl dichlorophosphate (0.42 ml) in 10 ml of tetrahydrofuran at −75° C. and stirred for 1 hour. The resulting mixture was then poured into a rapidly stirring suspension of 30 ml of pH 6 phosphate and 30 ml of dioxane at 0° C. The reaction mixture was stirred at ambient temperature for 1 hour and then placed at 5° C. overnight. Evaporation of the volatiles followed by chromatography on HP-20 resin yielded 400 mg, of the title compound.

(B)
(3S(Z))-3-[[(2-Amino-4-thiazolyl)(methoxyimino)acetyl]amino]-2-oxo-1-azetidinyl]phosphonic acid, 2,2,2-trifluoroethyl ester Diisopropylethylamine (0.115 ml) was added to a 121 mg of (Z)-2-amino-α-(methoxyimino)-4-thiazoleacetic acid (121 mg) in 2 ml of dimethylformamide at 23° C. The mixture was cooled to −20° C., diphenylphosphinyl chloride (0.110 ml) was added, and the resulting mixture was stirred for 2 hours to give a mixed anhydride. (S)-[3-[[(1,1-Dimethylethoxy)carbonyl]amino]-2-oxo-1-azetidinyl]phosphonic acid, 2,2,2-trifluoroethyl ester, potassium salt (232 mg) was suspended in 0.3 ml of anisole and cooled to 0° C. Trifluoroacetic acid (3 ml) was added, and the resulting mixture was stirred at 0° C. for 1 hour. The volatiles were evaporated and the residue was triturated with petroleum ether and anhydrous ether to yield the trifluoroacetic acid salt of (S)-(3-amino-2-oxo-1-azetidinyl)phosphonic acid, 2,2,2-trifluoroethyl ester as a powder. After evacuation for 1 hour, the residue was dissolved in 2 ml of dimethylformamide, and upon cooling to 0° C., 0.5 ml of diisopropylethylamine was added. The reaction mixture containing the mixed anhydride was then added to the azetidinone. After stirring at 5° C. overnight, the volatiles were removed under vacuum. The residue was purified by column chromatography with water on Dowex 50X2-400 resin (K⊕ form) followed by chromatography on HP-20 resin (eluting with water) to yield 74 mg of the title compound, melting point 175° C., dec.

EXAMPLE 33

[3S(Z)]-2-[[[1-(2-Amino-4-thiazolyl)-2-[[1-[hydroxy(2,2,2-trifluoroethoxy)phosphinyl]-2-oxo-3-azetidinyl]amino]-2-oxoethylidene]amino]oxy]-2-methylpropanoic acid, dipotassium salt (A)
[3S(Z)]-2-[[[1-(2-Amino-4-thiazolyl)-2-[[1-[hydroxy(2,2,2-trifluoroethoxy)phosphinyl]2-oxo-3-azetidinyl]amino]-2-oxoethylidene]amino]oxy]-2-methylpropanoic acid, benzhydryl ester Diisopropylethylamine (0.115 ml) was added to (Z)-2-amino-α-[[2-(diphenylmethoxy)-1,1-dimethyl-2-oxoethoxy]imino]-4-thiazoleacetic acid (278 mg) in 2 ml of dimethylformamide at 23° C. The mixture was cooled to −20° C., diphenylphosphinyl chloride (0.110 ml) was added, and the resulting mixture was stirred for 2.5 hours to give a mixed anhydride.

(S)-[3-[[(1,1-Dimethylethoxy)carbonyl]amino]-2-oxo-1-azetidinyl]phosphonic acid, 2,2,2-trifluoroethyl ester, potassium salt (232 mg; see example 32A) was dissolved in 0.3 ml of anisole and cooled to 0° C. Trifluoroacetic acid (3 ml) was added, and the resulting mixture was stirred at 0° C. for 1 hour. The volatiles were evaporated, and the residue was triturated with petroleum ether and anhydrous ether to yield the trifluoroacetic acid salt of (S)-(3-amino-2-oxo-1-azetidinyl)phosphonic acid, 2,2,2-trifluoroethyl ester as a powder. After evacuation for 0.5 hour, the residue was dissolved in 2 ml of dimethylformamide, and upon cooling to 0° C., 0.5 ml of diisopropylethylamine was added. The reaction mixture containing the mixed anhydride was then added to the azetidinone.

After stirring at 5° C. overnight, the volatiles were removed under vacuum. The residue was purified by column chromatography on Dowex 50X2-400 resin (K⊕ form) followed by chromatography on HP-20 (eluting with 40% acetone-water) to yield 223 mg of the title compound.

(B)
[3S(Z)]-2-[[[1-(2-Amino-4-thiazolyl)-2-[[1-[hydroxy(2,2,2-trifluoroethoxy)phosphinyl]-2-oxo-3-azetidinyl]amino]-2-oxoethylidene]amino]oxy]-2-methylpropanoic acid, dipotassium salt

[3S(Z)]-2-[1-(2-Amino-4-thiazolyl)-2-[[1-[hydroxy(2,2,2-trifluoroethoxy)phosphinyl]-2-oxo-3-azetidinyl- ]amino]-2-oxoethylidene]amino]oxy]-2-methylpropanoic acid, benzhydryl ester (223 mg) was dissolved in 1.5 ml of anisole and cooled to 0° C. Trifluoroacetic acid (3 ml) was added, and the resulting mixture was stirred at 0° C. for 2 hours. The volatiles were evaporated, and the residue was triturated with petroleum ether and anhydrous ether. The residue was dissolved in water, and the pH was adjusted to 7 with potassium bicarbonate. The residue was then purified by chromatography on HP-20 resin (eluting with water) to yield 131 mg of the title compound, melting point 200° C., dec.

EXAMPLE 34

[3S(Z)]-2-[[[1-(2-Amino-4-thiazolyl)-2-[[1-(butoxyhydroxyphosphinyl)-2-oxo-3-azetidinyl]amino]-2-oxoethylidene]amino]-2-methylpropanoic acid, dipotassium salt (A)

(S)-[2-Oxo-3-[[(1,1-dimethylethoxy)carbonyl]amino]-1-azetidinyl]phosphonic acid, n-butyl ester, potassium salt To phosphoryl chloride (50 ml) in 40 ml of carbon tetrachloride at ambient temperature was added dropwise n-butanol (29.65 g). After the initial exothermic reaction subsided, the reaction mixture was refluxed for 3 hours. Vacuum distillation at 88°–103° C. yielded 59.114 g of n-butyl dichlorophosphate.

A solution of (S)-3-[[(1,1-dimethylethoxy)carbonyl]amino]azetidin-2-one (1.116 g) in 40 ml of dry tetrahydrofuran at −78° C. was treated with 4.26 ml of 1.55 N n-butyl lithium. After 30 minutes, the reaction mixture was added to n-butyl dichlorophosphate (0.99 ml) in 20 ml of tetrahydrofuran at −78° C. and stirred for 1 hour. The resulting mixture was then poured into a rapidly stirring suspension of 30 ml of pH 6 phosphate and 30 ml of dioxane at 0° C. The reaction mixture was stirred at ambient temperature for 1 hour and then placed at 5° C. overnight. Evaporation of the volatiles followed by chromatography on HP-20 resin (eluting with water, 10% acetone-water, 20% acetone-water, and 40% acetone-water) yielded 850 mg of the title compound.

(B)

[3S(Z)]-2-[[[1-(2-Amino-4-thiazolyl)-2-[[1-(butoxyhydroxyphosphinyl)-2-oxo-3-azetidinyl]amino]-2-oxoethylidene]amino]oxy]-2-methylpropanoic acid, benzhydryl ester, potassium salt Diisopropylethylamine (0.115 ml) was added to 300 mg of (Z)-2-amino-α-[[2-(diphenylmethoxy)-1,1-dimethyl-2-oxoethoxy]imino]-4-thiazoleacetic acid (300 mg) in 2 ml of dimethylformamide at 23° C. The mixture was cooled to −20° C., diphenylphosphinyl chloride (0.110 ml) was added, and the resulting mixture was stirred for 2 hours to give a mixed anhydride.

(S)-[2-Oxo-3-[[(1,1-dimethylethoxy)carbonyl]amino]-1-azetidinyl]phosphonic acid, n-butyl ester, potassium salt (216 mg) was dissolved in 0.3 ml of anisole and cooled at 0° C. Trifluoroacetic acid (3 ml) was added, and the resulting mixture was stirred at 0° C. for 1 hour. The volatiles were evaporated and the residue was triturated with petroleum ether and anhydrous ether to yield the trifluoroacetic acid salt of (S)-(3-amino-2-oxo-1-azetidinyl)phosphonic acid, butyl ester as a powder. After evacuation for 1 hour, the residue was dissolved in 2 ml of dimethylformamide, and upon cooling to 0° C., 0.5 ml of diisopropylethylamine was added. The reaction mixture containing the mixed anhydride was then added to the azetidinone.

After stirring at 5° C. overnight, the volatiles were removed under vacuum. The residue was purified by column chromatography with water on Dowex 50X2-400 resin (K⊕ form) followed by chromatography on HP-20 resin (eluting with 40% acetone-water) to yield 180 mg of the title compound.

(C)

[3S(Z)]-2-[[[1-(2-Amino-4-thiazolyl)-2-[[1-(butoxyhydroxyphosphinyl)-2-oxo-3-azetidinyl]amino]2-oxoethylidene]amino]oxy]-2-methylpropanoic acid, dipotassium salt

[3S(Z)]-2-[[[1-(2-Amino-4-thiazolyl)-2-[[1-(butoxyhydroxyphosphinyl)-2-oxo-3-azetidinyl]amino]-2-oxoethylidene]amino]oxy]-2-methylpropanoic acid, benzhydryl ester potassium salt (180 mg) was dissolved in 1.5 ml of anisole and cooled to 0° C. Trifluoroacetic acid (3 ml) was added, and the resulting mixture was stirred at 0° C. for 2 hours. The volatiles were evaporated and the residue was triturated with petroleum ether and anhydrous ether. After evacuation for ½ hour, the residue was dissolved in water and the pH was adjusted to 7 by the addition of potassium bicarbonate. The residue was then purified by chromatography on HP-20 resin (eluting with water) to yield 82 mg of the title compound, melting point 180°–185° C., dec.

EXAMPLE 35

[3S(Z)]-[3-[[(2-Amino-4-thiazolyl)(methoxyimino)acetyl]amino]-2-oxo-1-azetidinyl]phosphonic acid, n-butyl ester, potassium salt Diisopropylethylamine (0.115 ml) was added to 121 mg of (Z)-2-amino-α-(methoxyimino)-4-thiazoleacetic acid (121 mg) in 2 ml of dimethylformamide at 23° C. The mixture was cooled to −20° C. and diphenylchlorophosphate (0.125 ml) was added, and the resulting mixture was stirred for ½ hour to yield a mixed anhydride.

(S)-[2-Oxo-3-[[(1,1-dimethylethoxy)carbonyl]amino]-1-azetidinyl]phosphonic acid, n-butyl ester, potassium salt (216 mg; see example 34A) was dissolved in 0.3 ml of anisole and cooled to 0° C. Trifluoroacetic acid (3 ml) was added, and the resulting mixture was stirred at 0° C. for 1 hour. The volatiles were evaporated and the residue was triturated with petroleum ether and anhydrous ether to yield the trifluoroacetic acid salt of (S)-(3-amino-2-oxo-1-azetidinyl)phosphonic acid, butyl ester. After evacuation for ½ hour, the residue was dissolved in 2 ml of dimethylformamide, and upon cooling to 0° C., 0.5 ml of diisopropylethylamine was added. The reaction mixture containing the mixed anhydride was then added to the azetidinone.

After stirring at 5° C. overnight, the volatiles were removed under vacuum. The residue was purified by column chromatography with water on Dowex 50X2-400 resin (K⊕ form) followed by chromatography on HP-20 resin (eluting with water and 10% acetone-water) to yield 130 mg of the title compound, melting point 178° C., dec.

EXAMPLE 36

[3S(Z)]-[3-[[(2-Amino-4-thiazolyl)(methoxyimino)acetyl]amino]-2-oxo-1-azetidinyl]phosphonic acid, phenyl ester, potassium salt (A)

(S)-[3-[[(1,1-Dimethylethoxy)carbonyl]amino]-2-oxo-1-azetidinyl]phosphonic acid, phenyl ester, potassium salt A solution of (S)-3-[[(1,1-dimethylethoxy)carbonyl]amino]-2-azetidinone (558 mg) in 20 ml of tetrahydrofuran at −78° C. was treated with 1.94 ml of 1.7 N n-butyl lithium. After 30 minutes the reaction mixture was added to phenyl dichlorophosphate (0.45 ml, 3.0 mmol) in 10 ml of tetrahydrofuran at −75° C. and stirred for 1 hour. The resulting mixture was then poured into a rapidly stirring suspension of 30 ml of pH 6 phosphate buffer and 30 ml of dioxane at 0° C. The reaction mixture was stirred at ambient temperature for 1 hour and then placed at 5° C. overnight. Evaporation of the volatiles followed by chromatography on HP-20 (eluting with water followed by 40% acetone-water) yielded 670 mg of the title compound.

(B)

[3S(Z)]-[3-[[(2-Amino-4-thiazolyl)(methoxyimino)acetyl]amino]-2-oxo-1-azetidinyl]phosphonic acid, phenyl ester, potassium salt Triethylamine (0.091 ml) was added to 121 mg of (Z)-2-amino-α-(methoxyimino)-4-thiazoleacetic acid (121 mg) in 2 ml of dimethylformaide at 23° C. The mixture was cooled to −20° C. and diphenyl chlorophosphate (0.123 ml) was added, and the resulting mixture was stirred for 45 minutes to yield a mixed anhydride.

(S)-[3-[[(1,1-Dimethylethoxy)carbonyl]amino]2-oxo-1-azetidinyl]phosphonic acid, phenyl ester, potassium salt (228 mg) was dissolved in 0.3 ml of anisole and cooled to 0° C. Trifluoroacetic acid (3 ml) was added, and the resulting mixture was stirred at 0° C. for 1 hour. The volatiles were evaporated and the residue was triturated with petroleum ether and anhydrous ether to yield the trifluoroacetic acid salt of 3-amino-2-oxo-1-azetidinylphosphonic acid, phenyl ester as a powder. After evacuation for 1 hour, the residue was dissolved in 2 ml of water, and upon cooling to 5° C. the pH was adjusted to ca.7 with solid potassium bicarbonate. The reaction mixture containing the mixed anhydride was then added to the azetidinone, and the pH was maintained at 7.0–7.3 with potassium bicarbonate and dilute hydrochloric acid.

After stirring at 5° C. overnight, the volatiles were removed under vacuum. The residue was purified by column chromatography with water on Dowex 50X2-400 resin (K⊕ form) followed by chromatography on HP-20 (eluting with water followed by 10% acetone-water) to yield 96 mg of the title compound (containing ca. 3 equivalent of potassium diphenyl phosphate).

EXAMPLE 37

[3S-[3α(Z),4β]]-2-[[[1-(2-Amino-4-thiazolyl)-2-[[4-methyl-2-oxo-1-(hydroxymethoxyphosphinyl)-3-azetidinyl]amino]-2-oxoethylidene]amino]oxy]-2-methylpropanoic acid (A)

(3S-trans)-4-Methyl-2-oxo-3-[[(1,1-dimethylethoxy)carbonyl]amino]-1-azetidinyl]phosphonic acid, dimethyl ester (3S-trans)-3-[[(1,1-Dimethylethoxy)carbonyl]amino]-4-methyl-2-azetidinone (5.0 g) dissolved in dry tetrahydrofuran (75 ml) was cooled to −78° C. under an inert atmosphere and 1.56 N n-butyl lithium in hexane (16 ml) was added while stirring. After several minutes dimethyl phosphorochloridate (3.0 ml) was added and the mixture was stirred at −78° C. for 1.5 hours. Phosphate buffer (0.5 M, pH 5.5, 100 ml) and saturated sodium chloride solution (100 ml) were added and the mixture was extracted three times with ethyl acetate. The combined extracts were dried (Na$_2$SO$_4$) and solvent was removed in vacuo yielding an oil which crystallized from ethyl acetate-ether-hexane (5.2 g, melting point 89°–94° C.). Chromatography of the solid on 125 g of silica gel using rapid elution with ethyl acetate yielded the title compound as an oil, which crystallized from etherpentane yielding 4.4 g, melting point 97.5°–98.5° C.

(B)

(3S-trans)-[4-Methyl-2-oxo-3-[[(1,1-dimethylethoxy)-carbonyl]amino]-1-azetidinyl]phosphonic acid, methyl ester, thiuronium salt (3S-trans)-[4-Methyl-2-oxo-3-[[(1,1-dimethylethoxy)-carbonyl]amino]-1-azetidinyl]phosphonic acid, dimethyl ester (4.25 g) and thiourea (1.05 g) were refluxed in acetonitrile (50 ml) under a nitrogen atmosphere for 24 hours. On cooling, the title compound crystallized, was collected by filtration and washed with cold acetonitrile followed by ether. After drying in vacuo, the title compound was obtained as a powder (4.68 g), melting point 168°–169° C.

(C)

(3S-trans)-[4-Methyl-2-oxo-3-[[(1,1-dimethylethoxy)-carbonyl]amino]-1-azetidinyl]phosphonic acid, methyl ester, potassium salt A solution of (3S-trans)-[4-methyl-2-oxo-3-[[(1,1-dimethylethoxy)carbonyl]amino]-1-azetidinyl]phosphonic acid, methyl ester, thiuronium salt (4.40 g) in water was passed through 110 ml of ion-exchange resin (Dowex 50X2-400, K⊕ form, 0.7 meq/ml). Removal of water in vacuo followed by slurrying with acetonitrile and removal of solvent under reduced pressure gave a semi-solid residue. Trituration with acetone-ether followed by ether yielded 3.83 g of the title compound as a powder.

(D)

(3S-trans)-[3-Amino-4-methyl-2-oxo-1-azetidinyl)phosphonic acid, methyl ester, trifluoroacetate salt (3S-trans)-[4-Methyl-2-oxo-3-[[(1,1-dimethylethoxy)-carbonyl]amino]-1-azetidinyl]phosphonic aicd, methyl ester, potassium salt (300 mg) suspended in dry anisole (0.3 ml), under a nitrogen atmosphere, was cooled to 0°–5° C. and trifluoracetic acid (3 ml) was added while stirring. After 1.25 hours, trifluoroacetic acid was removed in vacuo without heating and residual acid was chased under reduced pressure with toluene. The residual oil was solidified and triturated with ether yielding a powder.

(E)

[3S-[3α(Z),4β]]-2-[[[1-(2-Amino-4-thiazolyl)-2-[(4-methyl-2-oxo-1-(hydroxymethoxyphosphinyl)-3-azetidinyl)amino]-2-oxoethylidene]amino]oxy]-2-methylpropanoic acid, benzhydryl ester A mixed anhydride was formed by dissolving (Z)-2-amino-α-[[2-(diphenylmethoxy)-1,1-dimethyl-2-oxoethoxy]imino]-4-thiazoleacetic acid (containing 0.4 equivalents of isopropanol)(544 mg) and triethylamine (162 μl) in dry tetrahydrofuran (5 ml), cooling in an ice-methanol bath at −24° C., and adding diphenyl phosphorochloridate (242 μl). After stirring the mixture in the cooling bath for 20 minutes it was poured into a solution of (3S-trans)-[3-amino-4-methyl-2-oxo-1-azetidinyl)phosphonic acid, methyl ester, trifluoroacetate salt dissolved in water (5 ml) and adjusted to pH 7 with 5% potassium bicarbonate solution while cooling in an ice bath. Tetrahydrofuran (4 ml) was used to wash the anhydride into the reaction vessel. While maintaining the pH at 6.5–8.0 the mixture was stirred at 0°–5° C. for 3.5 hours and then at room temperature for 2 hours. Solvent was removed in vacuo, the residue was taken up in water and the pH was lowered to 2 with 1N hydrochloric acid. The resulting precipitate was collected by centrifugation, washed with water and dried. The solid was triturated with acetone-ether and ether, and dried, yielding 530 mg of the title compound containing ca. 0.5 equivalents of the side-chain acid.

(F)

[3S-[3α(Z),4β]]-2-[[[1-(2-Amino-4-thiazolyl)-2-[[4-methyl-2-oxo-1-(hydroxymethoxyphosphinyl)-3-azetidinyl]amino]-2-oxoethylidene]amino]oxy]-2-methylpropanoic acid

[3S-[3α(Z),4β]]-2-[[[1-(2-Amino-4-thiazolyl)-2-[(4-methyl-2-oxo-1-(hydroxymethoxyphosphinyl)-3-azetidinyl)amino]-2-oxoethylidene]amino]oxy]-2-methylpropanoic acid, benzhydryl ester (507 mg) was suspended in dry anisole (3 ml), cooled in an ice bath under a nitrogen atmosphere, and trifluoroacetic acid (6 ml) was added with stirring, thereby dissolving the solid. After 2 hours, dry toluene (10 ml) was added and solvent was removed in vacuo without heating. The residual oil was solidified and triturated three times with ether. The powder was suspended in water, and was dissolved by raising the pH to 2.5 with dilute potassium carbonate solution. After filtration and concentration in vacuo, the pH, which had risen to 2.8, was lowered to 2.4 with dilute trifluoroacetic acid. The acidic solution was chromatographed on HP-20 resin (100 ml) and the product was eluted with 10% acetone .90% water. Removal of solvent, followed by trituration with ether and drying yielded the title product (235 mg; melting point 187.5°–193° C. (dec.).

EXAMPLE 38

[3S-[3α(R),4β]]-3-[(Aminophenylacetyl)amino]-4-methyl-2-oxo-1-azetidinyl]phosphonic acid, methyl ester (A)

[3S-[3α(R),4β]]-3-[[[[[(p-Methoxyphenyl)methyl]oxy]carbonyl]amino](phenyl)acetyl]amino]-4-methyl-2-oxo-1-azetidinyl]phosphonic acid, methyl ester, potassium salt A solution of 1-hydroxybenzotriazole (766 mg) and p-methoxybenzyloxycarbonyl phenylglycine, in 12 ml of dry dimethylformamide was cooled to 0° C. and treated with dicyclohexylcarbodiimide (1.03 g). The mixture was stirred at 0° C. for 30 minutes. (3S-trans)-[3-Amino-4-methyl-2-oxo-1-azetidinyl)phosphonic acid, methyl ester, trifluoroacetate salt (2.07 g; see example 37D) was treated with 1 equivalent of triethylamine (454 mg) in 6 ml of dry dimethylformamide and the solution was added to the reaction mixture. The pH was maintained between 6.5 and 7.0 by adding triethylamine as necessary. The reaction was stirred at 0° C. for 30 minutes, and then at ambient temperature for 18 hours. The dimethylformamide was evaporated in vacuo at 30° C., and the residue was slurried in acetone to precipitate dicyclohexylurea. The solid was removed and washed with three 5 ml portions of acetone. The acetone solutions were combined and concentrated in vacuo yielding an oily residue. The oil was dissolved in 6 ml of 30% acetone-water applied to a column of 75 ml of Dowex 50X2-400 (K⊕) resin and eluted with 30% acetone-water to yield 2.36 g of impure potassium salt. The potassium salt was applied to a 200 ml column of HP-20 resin in water. Sequential elution with water, 5% acetone in water, 10% acetone in water, and finally 20% acetone in water provided 1.28 g of impure material.

(B)

[3S-[3α(R),4β]]-3-[(Aminophenylacetyl)amino]-4-methyl-2-oxo-1-azetidinyl]phosphonic acid, methyl ester

[3S-[3α(R),4β]]-3-[[[[[(p-Methoxyphenyl)methyl]oxy]carbonyl]amino](phenyl)acetyl]amino]-4-methyl-2-oxo-1-azetidinyl]phosphonic acid, methyl ester, potassium salt (1.28 g) was suspended in dry anisole (25 ml) and cooled to 0° C. in an ice-bath under nitrogen. Distilled trifluoroacetic acid (50 ml) was added and stirring at 0° C. was continued for 3.5 hours. The reaction was diluted with 50 ml of distilled toluene and the solvents were removed in vacuo without heating yielding a semi-solid. Toluene (40 ml) was added again and removal in vacuo yielded a solid (1.41 g). The solid was dissolved in 5 ml of water and the pH of the mixture raised to pH 4 by adding 5% potassium bicarbonate solution. The solution was then applied to a 200 ml column of HP-20 resin in water. Elution with water followed by lyophilization yielded 98 mg of the title compound as a solid.

Anal. calc'd for $C_{13}H_{18}N_3O_5P.0.4H_2O$: C, 46.75; H, 5.66; N, 12.58. found: C, 46.75; H, 5.67; N, 12.51.

EXAMPLE 39

[3S-[3α(Z),4β]]-3-[[(2-Amino-4-thiazolyl)(methoxyimino)acetyl]amino]-4-methyl-2-oxo-1-azetidinyl]phosphonic acid, methyl ester, potassium salt (3S-trans)-[4-Methyl-2-oxo-3-[[(1,1-dimethylethoxy)carbonyl]amino]-1-azetidinyl]phosphonic acid, methyl ester, potassium salt (55 mg; see example 37C) was dissolved in 96–98% formic acid (2 ml) and stirred overnight at room temperature. Removal of solvent in vacuo gave (3S-trans)-(3-amino-4-methyl-2-oxo-1-azetidinyl)phosphonic acid, methyl ester containing potassium formate.

(Z)-2-Amino-α-(methoxyimino)-4-thiazoleacetic acid (40 mg) and triethylamine (28 μl) were dissolved in dry dimethylformamide (1.5 ml), cooled in an ice-methanol bath (−20° C.) and diphenyl phosphorochloridate (41 μl) was added to form a mixed anhydride. After ca. 0.5 hour of stirring at −15° to −20° C., the mixture was added to a solution of the above-formed azetidinone in water and cooled in an ice-bath. Triethylamine (28 μl) was added, the mixture was stirred with cooling for 4.5 hours, and a second batch of mixed anhydride and triethylamine were added; stirring was continued overnight at 0°–5° C. Solvent was removed in vacuo, the oily residue was diluted with water and after standing for 1 day at 0°–5° C. a solid (the side-chain acid) was removed by filtration. The filtrate was passed through an ion-exchange resin (5 ml, Dowex 50X2-400, K⊕ form) and chromatographed on HP-20 resin (12 ml). The title compound (30 mg) was eluted with water and solidified with acetonitrile. After trituration with ether and drying, the title compound was obtained as a powder.

Anal. calc'd for $C_{11}H_{15}N_5O_6PSK$: C, 31.80; H, 3.64; N, 16.86. Found: C, 32.30; H, 3.97; N, 16.05.

EXAMPLE 40

[3S-[3α(Z),4β]]-[[[1-(2-Amino-4-thiazolyl)-2-[[1-(hydroxymethylphosphinyl)-4-methyl-2-oxo-3-azetidinyl]amino]-2-oxoethylidene]amino]oxy]acetic acid, dipotassium salt Following the procedure of example 37, but substituting (Z)-2-amino-α-[[2-(diphenylmethoxy)-2-oxoethoxy]imino]-4-thiazoleacetic acid for (Z)-2-amino-α-[[2-(diphenylmethoxy)-1,1-dimethyl-2-oxoethoxy]imino]-4-thiazoleacetic acid, yielded the title compound.

Anal calc'd for $C_{12}H_{14}N_5O_8P_5K_2$: C, 28.97; H, 2.84; N, 14.08; P, 6.23. Found: C, 26.15; H, 2.42; N, 11.54; P, 4.9.

EXAMPLE 41

[3S-[3α(Z),4β]]-2-[[[1-(2-Amino-4-thiazolyl)-2-[[1-(hydroxyethoxyphosphinyl)-4-methyl-2-oxo-3-azetidinyl]amino]-2-oxoethylidene]amino]oxy]-2-methylpropanoic acid, dipotassium salt

(A)

(3S-trans)-[4-Methyl-2-oxo-3-[[(1,1-dimethylethoxy)carbonyl]amino]-1-azetidinyl]phosphonic acid, diethyl ester (3S-trans)-3-[[(1,1-Dimethylethoxy)carbonyl]amino]-4-methyl-2-azetidinone (4.6 g) was dissolved in 75 ml of dry tetrahydrofuran and cooled to −78° C. in a dry ice-acetone bath under a nitrogen atmosphere, and was treated with 1.56 M n-butyl lithium (14.8 ml, 1 equivalent). The mixture was stirred for 30 minutes at −78° C. and then diethylphosphorochloridate (3.97 g) was added and stirring continued for 1 hour. The mixture was poured into saturated sodium chloride solution (60 ml) and extracted with ethyl acetate (three 40 ml portions). The extracts were combined and dried over anhydrous $Na_2SO_4$ and the solvent removed in vacuo. The residue was chromatographed on 125 g of silica gel eluted with ethyl acetate. Removal of solvent in vacuo followed by trituration with ether and drying yielding 4.72 g of the title compound, melting point 101°–103.5° C.

(B)

(3S-trans)-[4-Methyl-2-oxo-3-[[(1,1-dimethylethoxy)carbonyl]amino]-1-azetidinyl]phosphonic acid, ethyl ester, potassium salt A solution of the (3S-trans)-[4-methyl-2-oxo-3-[[(1,1-dimethylethoxy)carbonyl]amino]-1-azetidinyl]phosphonic acid, diethyl ester (1.0 g) was dissolved in acetonitrile (18 ml), thiourea (5 equivalents, 1.13 g) was added, and the mixture was refluxed under a nitrogen atmosphere for 60 hours. Solvent was removed in vacuo and the residue was dissolved in water. Passage of the solution through a 50 ml column of Dowex (K⊕ form) ion exchange resin, followed by removal of water in vacuo from the eluate gave the title potassium salt as an oil. The oily residue was applied to a 100 ml column of HP-20 resin in water. Elution with water and lyophilization yielded 560 mg of the title compound as a powder.

(C)

(3S-trans)-(3-Amino-4-methyl-2-oxo-1-azetidinyl)phosphonic acid, ethyl ester, trifluoroacetate salt A suspension of (3S-trans)-[4-methyl-2-oxo-3-[[(1,1-dimethylethoxy)carbonyl]amino]-1-azetidinyl]phosphonic acid, ethyl ester, potassium salt (500 mg) in anisole (5 ml) was cooled to −24° C. in an ice-methanol bath, and trifluoroacetic acid (10 ml) was added. The mixture was stirred at −24° C. to −12° C. for 3 hours, diluted with dry toluene (25 ml), and solvent was removed in vacuo at or below 19° C. The residual oil was solidified and triturated several times with ether giving 815 mg of the title compound as a powder.

(D)

[3S-[3α(Z),4β]]-2-[[[1-(2-Amino-4-thiazolyl)-2-[[1-(hydroxyethoxyphosphinyl)-2-methyl-4-oxo-3-azetidinyl]amino]-2-oxoethylidene]amino]oxy]-2-methylpropanoic acid, benzhydryl ester, potassium salt A solution of 1-hydroxybenzotriazole (230 mg) and (Z)-2-amino-α-[[2-(diphenylmethoxy)-1,1-dimethyl-2-oxoethoxy]imino-4-thiazoleacetic acid (750 mg) in 5 ml of dry dimethylformamide was cooled to 0° C. and treated with dicyclohexylcarbodiimide (310 mg). This mixture was stirred at 0° C. for 30 minutes. (3S-trans)-(3-Amino-4-methyl-2-oxo-1-azetidinyl)phosphonic acid, ethyl ester, trifluoroacetate salt (793 mg) was treated with 1 equivalent of triethylamine (151 mg) in 5 ml of dimethylformamide and was added to the reaction mixture; the pH was maintained between 6.5 and 7.0 by adding triethylamine as necessary. The reaction was stirred at 0° C. for 30 minutes and then at ambient temperature for 16 hours. The pH of the reaction was found to have fallen to 5.4 and was readjusted to 6.8 with triethylamine. An additional portion of active ester was prepared; a solution of 1-hydroxybenzotriazole (230 mg) and (Z)-2-amino-α-[[2-(diphenylmethoxy)1,1-dimethyl-2-oxoethoxy]imino-4-thiazoleacetic acid (750 mg) in 5 ml of dry dimethylformamide was cooled to 0° C. and treated with dicyclohexylcarbodiimide (310 mg). This mixture was stirred at 0° C. for 30 minutes and was added to the mixture containing the (3S-trans)-(3-amino-4-methyl-2-oxo-1-azetidinyl)phosphonic acid, ethyl ester, trifluoroacetate salt. Stirring was continued for 18 hours at room temperature keeping the pH between 6.5 and 7.0. The precipitated dicyclohexylurea was filtered and the dimethylformamide removed in vacuo yielding an oil. The residue was dissolved in water (6 ml) and the insoluble dicyclohexylurea filtered. The solution was applied to a 75 ml Dowex 50X2-400 (K⊕) ion-exchange column eluting with water and yielded 720 mg of impure potassium salt. The potassium salt was dissolved in 4 ml of water and applied to a 100 ml column of HP-20 resin in water. Sequential elution with water, 10% acetone in water, 20% acetone in water, and finally 30% acetone in water provided 228 mg of the title compound.

(E)

[3S-[3α(Z),4β]]-2-[[[1-(2-Amino-4-thiazolyl)-2-[[1-(hydroxyethoxyphosphinyl)-4-methyl-2-oxo-3-azetidinyl]amino]-2-oxoethylidene]amino]oxy]-2-methylpropanoic acid, dipotassium salt

[3S-[3α(Z),4β]]-2-[[[1-(2-Amino-4-thiazolyl)-2-[[1-(hydroxyethoxyphosphinyl)-2-methyl-4-oxo-3-azetidinyl]amino]-2-oxoethylidene]amino]oxy]-2-methylpropanoic acid, benzhydryl ester, potassium salt (220 mg) was suspended in dry anisole (10 ml) and cooled to 0° C. in an ice bath under nitrogen. Distilled trifluoroacetic acid (15 ml) was added and stirring at 0° C. was continued for 3.5 hours. The reaction was diluted with 25 ml of distilled toluene and the solvents were removed in vacuo without heating yielding a solid. The solid was dissolved in 4 ml of water and the pH adjusted to 6.8 with dilute potassium bicarbonate solution, and then applied to a 100 ml column of HP-20 resin in water. Elution with water followed by lyophilization yielded 158 mg of the title compound as a solid; N.M.R. (D$_2$O) shows material is an etherate. Fluorine analysis indicates the presence of 6.1% potassium trifluoroacetate.

Anal. Calc'd. for $C_{15}H_{20}N_5O_8PS.2K$: C, 33.39; H, 3.74; N, 12.98. Found: C, 27.54; H, 3.18; N, 7.81; F, 12.07.

EXAMPLE 42

[3S-[3α(Z),4β]]-3-[[(2-Amino-4-thiazolyl)(methoxyimino)acetyl]amino]-2-methyl-4-oxo-1-azetidinyl]-phosphonic acid, ethyl ester, potassium salt A solution of 1-hydroxybenzotriazole (222 mg) and Z-2-amino-α-(methoxyimino)-4-thiazoleacetic acid (292 mg) in 6 ml of dry dimethylformamide was cooled to 0° C. and treated with dicyclohexylcarbodiimide (329 mg), stirring at 0° C. for 30 minutes. (3S-trans)-[3-Amino-4-methyl-2-oxo-1-azetidinyl)phosphonic acid, ethyl ester, trifluoroacetate salt (520 mg; see example 41C) was treated with 1 equivalent of triethylamine (146 mg) in 4 ml of dry dimethylformamide at 0° C. and the solution was added to the reaction mixture, maintaining the pH between 6.5 and 7.0 by the addition of triethylamine as required. The reaction was stirred at 0° C. for 30 minutes, and then at ambient temperature for 18 hours. The dimethylformamide was evaporated in vacuo at 30° C., and the residue was taken up in 4 ml of water. The insoluble dicyclohexylurea was removed and the solution applied to a column of 50 ml of Dowex 50X2-400 (K⊕) resin eluting with water yielding 310 mg of potassium salt. A 300 mg portion of the potassium salt was applied to a 75 ml column of HP-20 resin in water. Elution with water gave 130 mg of the title compound as a solid, melting point 154°–156° C., dec.

Anal. Calc'd for $C_{12}H_{17}N_5O_6PSK.1H_2O$: C, 32.09; H, 4.31; N, 15.59; P, 6.9. Found: C, 32.09; H, 4.17; N, 15.37; P, 6.9.

EXAMPLE 43

[3S-[3α(Z),4β]]-3-[[(2-Amino-4-thiazolyl)(methoxyimino)acetyl]amino]-4-methyl-2-oxo-1-azetidinyl]-phosphonic acid, diethyl ester (A)

(3S-trans)-(3-Amino-4-methyl-2-oxo-1-azetidinyl)phosphonic acid, diethyl ester, trifluoroacetic acid salt (3S-trans)-[4-Methyl-2-oxo-3-[[(1,1-dimethylethoxy)-carbonyl]amino]-1-azetidinyl]phosphonic acid, diethyl ester (1.0 g; see example 41A) was suspended in dry anisole (10 ml) and cooled to 0° C. in an ice bath under nitrogen. Distilled trifluoroacetic acid (15 ml) was added and stirring at 0° C. was continued for 3.5 hours. The reaction was diluted with 25 ml of distilled toluene and the solvents were removed in vacuo without heating yielding a solid. Toluene was again added (two 25 ml portions) and removed in vacuo and the resulting solid triturated with anhydrous ether (30 ml). The solid was dried in vacuo at room temperature yielding 1.0 g of the title salt.

(B)

[3S-[3α(Z),4β]]-3-[[(2-Amino-4-thiazolyl)(methoxyimino)acetyl]amino]-4-methyl-2-oxo-1-azetidinyl]-phosphonic acid, diethyl ester A solution of 1-hydroxybenzotria±ole (475 mg) and (Z)-2-amino-α-(methoxyimino)-4-thiazoleacetic acid (624 mg) in 12 ml of dry dimethylformamide was cooled to 0° C. and treated with dicyclohexylcarbodiimide n(1053 mg), stirring at 0° C. for 30 minutes. (3S-trans)-(3-Amino-4-methyl-2-oxo-1-azetidinyl)phosphonic acid, diethyl ester, trifluoroacetic acid salt was treated with 1 equivalent of triethylamine (303 mg) in 8 ml of dimethylformamide and the solution was added to the reaction mixture. The pH was maintained between 6.5 and 7.0 by adding triethylamine as required. The reaction was stirred for 30 minutes at 0° C. and then overnight at ambient temperature. The dimethylformamide was removed in vacuo at 30° C., and the residue was dissolved in 6 ml of ethyl acetate and applied to a 250 ml column of CC-4 silica gel. Elution with 10% ethanol in ethyl acetate followed by elution with 25% ethanol in ethyl acetate provided 380 mg of an oily residue. The residue was crystallized twice from ethyl acetate yielding 110 mg of the title compound as a solid, melting point 110°–112° C.

Anal. Calc'd for $C_{14}H_{22}N_5SPO_6$: C, 40.09; H, 5.29; N, 16.70; P, 7.4. Found: C, 39.86; H, 5.26; N, 16.61; P, 7.4.

EXAMPLE 44

[3S-[3α(Z),4α]]-2-[[[1-(2-Amino-4-thiazolyl)-2-[[4-methyl-2-oxo-1-(hydroxymethoxyphosphinyl)-3-azetidinyl]amino]-2-oxoethylidene]amino]oxy]-2-methylpropanoic acid, dipotassium salt

(A)
(3S-cis)-[4-Methyl-2-oxo-3-[[(1,1-dimethylethoxy)carbonyl]amino]-1-azetidinyl]phosphonic acid, dimethyl ester (3S-cis)-3-[[(1,1-Dimethylethoxy)carbonyl]amino]-4-methyl-2-azetidinone (918 mg) dissolved in dry tetrahydrofuran (25 ml) was cooled to −78° C. under an inert atmosphere and 1.56 M n-butyl lithium (3 ml) was added while stirring. After thirty minutes dimethyl phosphorochloridate (3.0 ml) was added and the mixture was stirred at −78° C. for 2 hours. Saturated sodium chloride solution (20 ml) was added and the mixture allowed to warm to room temperature and extracted three times with 30 ml ethyl acetate portions. The combined extracts were dried (Na2SO4) and solvent was removed in vacuo yielding an oil. Chromatography of the oil dissolved in 4 ml of ethyl acetate on a 34 g silica gel column eluting with ethyl acetate yielded 875 mg of the title compound.

(B)
(3S-cis)-[4-Methyl-2-oxo-3-[[(1,1-dimethylethoxy)carbonyl]amino]-1-azetidinyl]phosphonic acid, methyl ester, potassium salt (3S-cis)-[4-Methyl-2-oxo-3-[[(1,1-dimethylethoxy)-carbonyl]amino]-1-azetidinyl]phosphonic acid, dimethyl ester (848 mg) and thiourea (210 mg) were refluxed in acetonitrile (8 ml) under a nitrogen atmosphere for 18 hours. Solvent was removed in vacuo and the residue was dissolved in water; passage of the solution through a 50 ml column of Dowex K⊕ ion exchange resin, followed by removal of water in vacuo from the eluate gave the potassium salt as an oil. The oily residue was applied to a 70 ml column of HP-20 resin in water. Elution with water, removal of the water in vacuo, and trituration with acetone yielded 380 mg of the title compound as a solid.

(C)
(3S-cis)-(3-Amino-4-methyl-2-oxo-1-azetidinyl)phosphonic acid, methyl ester, trifluoroacetate salt A suspension of (3S-cis)- [4-methyl-2-oxo-3-]](1,1-dimethylethoxy)carbonyl]amino]-1-azetidinyl]phosphonic acid, methyl ester, potassium salt (350 mg) in anisole (3 ml) was cooled to −24° C. in an ice-methanol bath, and trifluoroacetic acid (6 ml) was added. The mixture was stirred for 1.5 hours at −24° C., diluted with dry toluene (10 ml) and the solvents were removed in vacuo, at or below 19° C. The residual oil was solidified and triturated several times with ether giving 352 mg of the title compound.

(D)
[3S-[3α(Z),4α]]-2-[[[1-(2-Amino-4-thiazolyl)-2-[(4-methyl-2-oxo-1-(hydroxymethoxyphosphinyl)-3-azetidinyl)amino]-2-oxoethylidene]amino]oxy]-2-methylpropanoic acid, benzhydryl ester, potassium salt An active ester was formed by stirring (Z)-2-amino-α-[[2-(diphenylmethoxy)-1,1-dimethyl-2-oxoethoxy]imino]-4-thiazoleacetic acid (331 mg), N-hydroxybenzotriazole hydrate (110 mg) and dicyclohexylcarbodiimide (148 mg) in 4 ml of dimethylformamide for 1.5 hours at room temperature. (3S-cis)-[3-Amino-4-methyl-2-oxo-1-azetidinyl)phosphonic acid, methyl ester, trifluoroacetate salt in dimethylformamide (5 ml), pH adjusted with triethylamine to 6.5, was added to the mixture and stirred at room temperature overnight. Solvent was removed in vacuo, the residue was taken up in water, the pH was adjusted to 6.5 with dilute potassium bicarbonate, and the mixture was filtered to remove dicyclohexylurea. The solution was applied to a column of 75 ml of Dowex 50X2-400 (K⊕) ion exchange resin eluting with water giving 148 mg of impure potassium salt. The potassium salt was applied to a 100 ml column of HP-20 resin in water. A gradient of water (500 ml) and acetone-water (1:1, 500 ml) was used to elute the column yielding 72 mg of the title compound as a solid.

(E)
[3S-[3α(Z),4α]]-2-[[[1-(2-Amino-4-thiazolyl)-2-[[4-methyl-2-oxo-1-(hydroxymethoxyphosphinyl)-3-azetidinyl]amino]-2-oxoethylidine]amino]oxy]-2-methylpropanoic acid, dipotassium salt

[3S-[3α(Z),4α]]-2-[[[1-(2-Amino-4-thiazolyl)-2-[(4-methyl-2-oxo-1-(hydroxymethoxyphosphinyl)-3-azetidinyl)amino]-2-oxoethylidene]amino]oxy]-2-methyl propanoic acid, benzhydryl ester (58 mg) was suspended in anisole (2 ml), cooled in an ice-methanol bath at −24° C., and trifluoroacetic acid (4 ml) was added. The mixture was stirred at −24° C., for 2.5 hours, then diluted with dry benzene (10 ml); solvent was removed in vacuo. at, or below, 19° C. The residual oil was dissolved in water (4 ml) and the pH was adjusted to 6.8 with dilute potassium bicarbonate solution. The solution was applied to a 30 ml column of HP-20 resin in water and eluted with water. Lyophilization yielded 26 mg of the title compound as a solid.

EXAMPLE 45

[3S-[3α(Z),4α]]-[3-[[(2-Amino-4-thiazolyl)(methoxyimino)acetyl]amino]-2-methyl-4-oxo--1-azetidinyl]phosphonic acid, methyl ester, potassium salt A solution of 1-hydroxybenzotriazole (92 mg) and (Z)-2-amino-α-(methoxyimino)-4-thiazoleacetic acid (121 mg) in 2.5 ml of dry dimethylformamide was cooled to 0° C. in an ice bath and treated with dicyclohexylcarbodiimide (124 mg). This mixture was stirred at 0° C. for 30 minutes. At this time an amount of (3S-cis)-(3-amino-4-methyl-2-oxo-1-azetidinyl)phosphonic acid, methyl ester, trifluoroacetate salt (276 mg; see example 44C) was treated with 1 equivalent of triethylamine (61 mg) in 2.5 ml of dimethylformamide and was added to the reaction mixture, maintaining the pH of the mixture between pH 6.5 and 7 by adding triethylamine as required. The reaction was stirred at 0° C. for 30 minutes, and then at ambient temperature for 18 hours. The dimethylformamide was removed in vacuo at 30° C., and the residue was dissolved in 5 ml of water and the insoluble dicyclohexylurea filtered off. The solution was applied to a column of 40 ml of Dowex 50X2-400 (K⊕) and eluting with water yielded 210 mg of impure potassium salt. A 200 mg portion of this material was applied to a 40 ml column of HP-20 resin in water. Elution with water and lyophilization yielded 118 mg of the title compound as a solid.

Anal. Calc'd for $C_{11}H_{15}N_5SPO_6K+0.75H_2O$: C, 30.78; H, 3.88; N, 16.32; P, 7.2. Found: C, 30.78; H, 3.85; N, 16.12; P, 7.3.

EXAMPLE 46

[3S(Z)]-P-[3-[[(2-Amino-4-thiazolyl)(methoxyimino)acetyl]amino]-2-oxo-1-azetidinyl]-N-propylphosphonamidic acid, potassium salt (A)

(S)-P-[3-[[(Phenylmethoxy)carbonyl]amino]-2-oxo-1-azetidinyl]-N-propylphosphonamidic acid, methyl ester (S)-3-[[(Phenylmethoxy)carbonyl]amino]-2-azetidinone (5.0 g) was dissolved in dry tetrahydrofuran (140 ml) and cooled to −78° C. in a dry ice-acetone bath under a nitrogen atmosphere. This mixture was treated with 1 equivalent of a 1.56 M solution of n-butyl lithium in hexane (14.2 ml) and was stirred for 30 minutes at −78° C. Methyl dichlorophosphate (3.38 g) was added and the mixture stirred for 1 hour at −78° C., followed by the addition of 2 equivalents of distilled n-propylamine (2.68 g) and stirring for an additional 2 hours at −78° C. The reaction was treated with 0.5 M phosphate buffer pH 5.5 (150 ml), allowed to warm to 5° C., and extracted with three 125 ml portions of ethyl acetate. The extracts were combined, dried over anhydrous $Na_2SO_4$ and the solvent removed in vacuo yielding an oily residue. The residue was dissolved in acetonitrile (60 ml) and applied to 500 g column of silica gel eluting with acetonitrile. Removal of solvent in vacuo yielded 4.6 g of the title compound, melting point 121°-123° C.

(B)

(S)-P-[3-[[(Phenylmethoxy)carbonyl]amino]-2-oxo-1-azetidinyl]-N-propylphosphonoamidic acid, anilinium salt (S)-P-[3-[[(Phenylmethoxy)carbonyl]amino]-2-oxo-1-azetidinyl]-N-propylphosphonamidic acid, methyl ester, potassium salt (3.0 g) was dissolved in distilled dichloromethane (30 ml) and cooled to 0°-5° C. in an ice-bath under a nitrogen atmosphere. Bis(trimethylsilyl)acetamide (6.88 g) was added and the mixture stirred at 0° C. for 0.5 hour. Trimethylsilylbromide (3.9 g) was added and the mixture stirred for 3 hours at 0° to 5° C. The solvent and excess bis(trimethylsilyl)acetamide and trimethylsilylbromide were removed in vacuo. The oil was taken up in three 20 ml portions of dry toluene and the toluene was removed in vacuo yielding a pale residue. The residue was dissolved in dry tetrahydrofuran (50 ml) and 2 equivalents of distilled aniline (1.57 g) in absolute ethanol (15 ml) was added; the mixture was stirred at room temperature for 0.5 hour. The solvents were removed in vacuo yielding an oily residue which was dissolved in acetonitrile (100 ml) by heating to 80° C. The hot acetonitrile solution was filtered and stored in the freezer overnight (−10° C.). The title compound crystallized yielding 2.65 g of material, melting point 186°-190° C., dec.

(C)

(S)-P-(3-Amino-2-oxo-1-azetidinyl)-N-propylphosphonamidic acid

A solution of (S)-P-[3-[[(phenylmethoxy)carbonyl]amino]-2-oxo-1-azetidinyl]-N-propylphonoamidic acid, anilinium salt (2.5 g) in methanol (15 ml) was added to a pre-hydrogenated suspension of 10% palladium on charcoal (1.25 g) in methanol (50 ml). The mixture was vigorously stirred under a hydrogen atmosphere for 0.5 hour, the atmosphere was exchanged for fresh hydrogen, and stirring was continued for 1 hour. The catalyst was removed by filtering the mixture through Celite on a Millipore filter and the solvent was removed in vacuo yielding 0.78 g of the title compound as a solid.

(D)

[3S(Z)]-P-[3-[[(2-Amino-4-thiazolyl)(methoxyimino)acetyl]amino]-2-oxo-1-azetidinyl]-N-propylphosphonamidic acid, potassium salt A mixed anhydride was formed by stirring (Z)-2-amino-α-(methoxyimino)-4-thiazoleacetic acid (53 mg) and triethylamine (26.8 mg) in dry dimethylformamide (2 ml) under a nitrogen atmosphere. The mixture was cooled to 0° C. in an ice bath and diphenyl chlorophosphate (77.7 mg) was added and stirring continued for 1 hour at 0° C. (S)-P-(3-Amino-2-oxo-1-azetidinyl)-N-propylphosphonamidic acid (50 mg) in dimethylformamide (2 ml) was treated with triethylamine (24.4 mg), cooled to 0° C. and stirred under nitrogen. The mixed anhydride was added and the mixture stirred for 6 hours at 0° C. and then overnight at room temperature. The dimethylformamide was removed in vacuo, yielding an oily residue. The residue was dissolved in water (2 ml) and applied to a 10 ml column of Dowex 50X2-400 (K⊕) ion-exchange resin. Elution with water yielded 122 mg of impure potassium salt. The potassium salt was dissolved in water (2 ml) and applied to a 15 ml column of HP-20 resin in water. Elution with water and removal of water in vacuo yielded a glass-like residue which was triturated with acetone yielding 24 mg of the title compound as a solid, melting point 185° C., dec.

Anal. Calc'd. for $C_{12}H_{18}N_6SPO_5K.0.75H_2$: C, 32.64; H, 4.44; N, 19.04. Found: C, 32.64; H, 4.63; N, 19.01.

EXAMPLE 47

[3S-[3α(Z),4β]]-2-[[[1-(2-Amino-4-thiazolyl)-2-[[1-[[(2,2-dimethyl-1-oxopropoxy)methoxy]methoxyphosphinyl]-2-methyl-4-oxo-3-azetidinyl]amino]-2-oxoethylidene]amino]oxy]-2-methylpropanoic acid (A)

(3S-trans)-4-Methyl-2-oxo-3-[[(1,1-dimethylethoxy)carbonyl]amino]-1-azetidinyl]phosphonic acid, ethyl ester, potassium salt A solution of (3S-trans)-3-[[(1,1-dimethylethoxy)carbonyl]amino]-4-methyl-2-azetidinone (2.0 g) in 60 ml of dry tetrahydrofuran at −78° C. was treated with 6.40 ml (11 mmol) of 1.72 N n-butyl lithium. After 30 minutes, the reaction mixture was added to ethyl dichlorophosphate (1.31 ml, 11 mmol) in 30 ml of tetrahydrofuran at −78° C. and stirred for 1 hour. The resulting mixture was then poured into a rapidly stirring suspension of 100 ml of 0.36 N pH6 phosphate and 100 ml of dioxane at 0° C. The reaction mixture was stirred at ambient temperature for 30 minutes and then placed at 5° C. overnight. Evaporation of the volatiles followed by chromatography on HP-20 (eluting with water, 10% acetone-water, 20% acetone-water, and 40% acetonewater) yielded 1.61 g of the title compound.

(B)

(3S-trans)-[4-Methyl-2-oxo-3-[[(1,1-dimethylethoxy)carbonyl]amino]-1-azetidinyl]phosphonic acid, ethyl ester, tetrabutylammonium salt To 1.61 g of (3S-trans)-(4-methyl-2-oxo-3-[[(1,1-dimethylethoxy)carbonyl]amino]-1-azetidinyl]phosphonic acid, ethyl ester, potassium salt was added 100 ml of aqueous tetrabutylammonium hydrogen sulfate (3.40 g) previously adjusted to pH 6.3 with potassium bicarbonate. The aqueous solution was then extracted with eight 50 ml portions of methylene chloride. The combined organic extracts were dried with sodium sulfate, and the volatiles were evaporated to yield a viscous oil. Trituration with petroleum ether and ether provided the title compound as a waxy solid (1.85 g).

The tetrabutylammonium salt was further purified by column chromatography on HP-20 (eluting with water, 10% acetone-water, 20% acetone-water, 40% acetone-water) to yield 1.21 g of the title compound.

(C)
(3S-trans)-[4-Methyl-2-oxo-3-[[(1,1-dimethylethoxy)carbonyl]amino]-1-azetidinyl]phosphonic acid, methyl ester, tetrabutylammonium salt To (3S-trans)-[4-methyl-2-oxo-3-[[(1,1-dimethylethoxy)carbonyl]amino]-1-azetidinyl]phosphonic acid, methyl ester, potassium salt (2.055 g; see example 37C was added 25 ml of aqueous tetrabutylammonium hydrogen sulfate (2.32 g) previously adjusted to pH 6.3 with potassium bicarbonate. The aqueous solution was then extracted with nine 25 ml portions of dichloromethane. The combined organic extracts were then dried with sodium sulfate, and the volatiles were evaporated to yield a viscous oil. Trituration with petroleum ether and ether provided the title compound as a waxy solid (2.95 g).

(D)
(3S-trans)-[4-Methyl-2-oxo-3-[[(1,1-dimethylethoxy)carbonyl]amino]-1-azetidinyl]phosphonic acid, methyl ester, (2,2-dimethyl-1-oxopropoxy)methyl ester A solution of (3S-trans)-[4-methyl-2-oxo-3-[[(1,1-dimethylethoxy)carbonyl]amino]-1-azetidinyl]phosphonic acid, ethyl ester, tetrabutylammonium salt (1.12 g) and pivaloyloxymethyl chloride (0.59 ml) in 1,1,1-trichloroethane (21 ml) was refluxed overnight. The reaction mixture was cooled to room temperature and dimethyl sulfate (0.297 ml) was added. The reaction was stirred at room temperature for 2 days.

In the same fashion, a solution of (3S-trans)-[4-methyl-2-oxo-3-[[(1,1-dimethylethoxy)carbonyl]amino]-1-azetidinyl]phosphonic acid, methyl ester, tetrabutylammonium salt (3.22 g) was sequentially subjected to pivaloyloxymethyl chloride (1.8 ml) and dimethyl sulfate (0.88 ml) in 1,1,1-trichloroethane (60 ml).

The crude reaction mixtures were then combined and extracted once with 90 ml of pH 6 phosphate buffer. The aqueous layer was then extracted three times with ethyl acetate. The combined organic layers were washed with brine and dried over sodium sulfate. Evaporation of the solvents followed by silica gel column chromatography (eluting with 45% ethyl acetate-hexane followed by 100% ethyl acetate) gave 2.60 g of the title compound.

(E)
[3S-[3α(Z),4β]]-2-[[[1-(2-Amino-4-thiazolyl)-2-[[1-[[(2,2-dimethyl-1-oxopropoxy)methoxy]methoxyphosphinyl]-2-methyl-4-oxo-3-azetidinyl]amino]-2-oxoethylidene]amino]oxy]-2-methylpropanoic acid, benzhydryl ester Diisopropylethylamine (0.115 ml) was added to (Z)-(2-amino-α-[[2-(diphenylmethoxy)-1,1-dimethyl-2-oxoethoxy]imino]-4-thiazoleacetic acid (264 mg) in 2 ml of acetonitrile at room temperature. The mixture was cooled to −20° C., diphenyl chlorophosphate (0.124 ml) was added, and the resulting mixture was stirred for 30 minutes to give a mixed anhydride.

(3S-trans)-[4-Methyl-2-oxo-3-[[(1,1-dimethylethoxy)carbonyl]amino]-1-azetidinyl]phosphonic acid, methyl ester, (2,2-dimethyl-1-oxopropoxy)methyl ester (245 mg) was dissolved in 0.3 ml of anisole and cooled to 0° C. Trifluoroacetic acid (3 ml) was added, and the resulting mixture was stirred at 0° C. for 1 hour. The volatiles were evaporated, and the residue was triturated with petroleum ether and ether to yield the trifluoroacetic acid salt of (3S-trans)-(3amino-2-oxo-1-azetidinyl)phosphonic acid, methyl ester, pivaloyloxymethyl ester as a viscous oil. After evacuation for 2 hours, acetonitrile (2 ml) was added, and upon cooling to 0° C., 0.3 ml of diisopropylethylamine was added. The reaction mixture containing the mixed anhydride was then immediately added to the azetidinone.

After stirring at 5° C. for 2 hours, the reaction mixture was poured into aqueous potassium biphosphate and extracted three times with ethyl acetate. The combined organic layers were extracted once with aqueous sodium bicarbonate and once with water. Upon drying with sodium sulfate, the volatiles were removed to yield the title compound as a crude, viscous oil.

(F)
[3S-[3α(Z),4β]]-2-[[[1-(2-Amino-4-thiazolyl)-2-[[1-[[(2,2-dimethyl-1-oxopropoxy)methoxy]methoxyphosphinyl]-2-methyl-4-oxo-3-azetidinyl]amino]-2-oxoethylidene]amino]oxy]-2-methylpropanoic acid

[3S-[3α(Z),4β]]-2-[[[1-(2-Amino-4-thiazolyl)-2-[[1-[[(2,2-dimethyl-1-oxopropoxy)methoxy]methoxyphosphinyl]-2-methyl-4-oxo-3-azetidinyl]amino]-2-oxoethylidene]amino]oxy]-2-methylpropanoic acid, benzhydryl ester was dissolved in 1.5 ml of anisole and cooled to 0° C. Trifluoroacetic acid (3 ml) was added, and the resulting mixture was stirred at 0° C. for 90 minutes. The volatiles were evaporated, toluene was added, and the volatiles were removed again. The residue was dissolved in water-acetone and the pH was adjusted to 6.5 using concentrated potassium bicarbonate. Column chromatography on HP-20 (eluting with water, 10% acetone-water, 20% acetone-water, and 40% acetone-water) yielded, upon lyophilization, 192 mg of the potassium salt of the title compound.

The potassium salt was acidified to pH 2.5 with dilute hydrochloric acid. Column chromatography on HP-20 (eluting with water, 10% acetone-water, 20% acetone-water, 40% acetone-water, and 80% acetone-water) yielded, upon lyophilization 105 mg of the title compound, melting point 140° C., dec.

EXAMPLE 48

[3S-[3α(Z),4β]]-2-[[[1-(2-Amino-4-thiazolyl)-2-[[1-[[(2,2-dimethyl-1-oxopropoxy)methoxy]methoxyphosphinyl]-2-methyl-4-oxo-3-azetidinyl]amino]-2-oxoethylidene]amino]oxy]-2-methylpropanoic acid, potassium salt Diisopropylethylamine (0.199 ml) was added to (Z)-2-amino-α-[[2-(diphenylmethoxy)-1,1-dimethyl-2-oxoethoxy]imino]-4-thiazoleacetic acid (519 mg) in 3.5 ml of dimethylformamide at room temperature. The mixture was cooled to −20° C., diphenyl chlorophosphate (0.217 ml) was added, and the resulting mixture was stirred for 30 minutes to yield a mixed anhydride.

(S)-[3-[[(Benzyloxy)carbonyl]amino]-2-oxo-1-azetidinyl]phosphonic acid, (2,2-dimethyl-1-oxopropoxy)methyl ester (443 mg; see example 50C) was dissolved in 5.2 ml of dimethylformamide. The benzyloxycarbonyl protecting group was remove by catalytic hydrogenolysis over Pd/C (22 mg). The reaction mixture was placed under nitrogen and cooled to 0° C. Diisopropylethylamine (0.86 ml) was then added to the azetidinone followed by the mixed anhydride. After stirring at 5° C. overnight, the reaction mixture was poured into aqueous potassium phosphate buffer (pH ca. 5). The aqueous layer was extracted four times with ethyl acetate and the Pd/C catalyst was removed by filtration.

The combined ethyl acetate layers were extracted with water, with sodium bicarbonate, and again with water. The ethyl acetate layer was dried with sodium sulfate and the volatiles were removed to yield the crude diphenylmethyl ester of the title compound.

The crude diphenylmethyl ester was dissolved in 1.5 ml of anisole and cooled to 0° C. Trifluoroacetic acid (3 ml) was added, and the resulting mixture was stirred at 0° C. for one hour. The volatiles were evaporated, toluene was added, and the volatiles were removed again. The residue was triturated with petroleum ether and ether and evacuated. The residue was then dissolved in water-acetone and the pH was adjusted to 6.5 using aqueous potassium bicarbonate. Column chromatography on HP-20 resin (eluting with water, 10% acetone-water, 20% acetone-water, 30% acetone-water, and 40% acetone-water) yielded upon lyophilization, 67 mg of the title compound.

EXAMPLE 49

[3S-[3α(Z),4β]]-2-[[[1 (2-Amino-4-thiazolyl)-2-[[1-[(carboxymethoxy)hydroxyphosphinyl]-4-methyl-2-oxo-3-azetidinyl]amino]-2-oxoethylidene]amino]oxy]-2-methylpropanoic acid (A)

(3S-trans)-[3-[[(1,1-Dimethylethoxy)carbonyl]amino]-4-methyl-2-oxo-1-azetidinyl]phosphonic acid, [[(1,1-dimethylethoxy)carbonyl]methyl]ester, potassium salt A solution of (3S-trans)-[4-methyl-2-oxo-3-[[(1,1-dimethylethoxy)carbonyl]amino]-1-azetidinyl]phosphonic acid, methyl ester, tetrabutylammonium salt (1.41 g; see example 47C) and t-butylbromoacetate (0.850 ml) in 1,1,1-trichloroethane (24 ml) was refluxed overnight. The volatiles were evaporated, and the residue was subjected to a Dowex 50X2-400 (K⊕ form) column (eluting with water) followed by an HP-20 column (eluting with water, 10% acetone-water, 20% acetone-water, and 40% acetonewater) to yield 713 mg of the title compound.

(B)

[3S-[3α(Z),4β]]-2-[[[1-[2-Amino-4-thiazolyl)-2-[[1-[(carboxymethoxy)hydroxyphosphinyl]-4-methyl-2-oxo-3-azetidinyl]amino]-2-oxoethylidene]amino]oxy]-2-methylpropanic acid, diphenylmethyl ester, dipotassium salt Diisopropylethylamine (0.134 ml) (0.7 mmol) was added to (Z)-2-amino-o-[[2-(diphenylmethoxy)1,1-dimethyl-2-oxoethoxy]imino]-4-thiazoleacetic acid (308 mg) in 2 ml of acetonitrile at room temperature. The mixture was cooled to −20° C., diphenyl chlorophosphate (0.145 ml) was added, and the resulting mixture was stirred for 30 minutes to give a mixed anhydride.

(3S-trans)-[3-[[(1,1-Dimethylethoxy)carbonyl]amino]-4-methyl-2-oxo-1-azetidinyl]phosphonic acid, [[(1,1-dimethylethoxy)carbonyl]methyl]ester, potassium salt (260 mg) (0.6 mmol) was dissolved in 0.3 ml of anisole and cooled to 0° C. Trifluoroacetic acid (3 ml) was added, and the resulting mixture was stirred at 0° C. for 105 minutes. The volatiles were evaporated, and the residue was triturated with petroleum ether and anhydrous ether to yield the trifluoroacetic acid salt of (3S-trans)-3-amino-2-oxo-1-azetidinyl)phosphonic acid, carboxymethyl ester. After evacuation for 1 hour, the residue was dissolved in 2 ml of water and cooled to 0° C. The pH was adjusted to 6.95 with solid potassium bicarbonate, the mixed anhydride was added, and the reaction mixture was stirred at 5° C. overnight.

The volatiles were removed under vacuum. The residue was purified by column chromatography with water on Dowex 50X2-400 resin (K⊕ form) followed by chromatography on HP-20 (eluting with water, 10% acetone-water, 20% acetone-water, and 40% acetone-water) to give the title compound.

(C)

[3S-[3α(Z),4β]]-2-[[[1-[2-Amino-4-thiazolyl)-2-[[1-[(carboxymethoxy)hydroxyphosphinyl]-4-methyl-2-oxo-3-azetidinyl]amino]-2-oxoethylidene]-amino]oxy]-2-methylpropanoic acid

[3S-[3α(Z),4β]]-2-[[[1-[2-Amino-4-thiazolyl)-2-[[1-[(carboxymethoxy)hydroxyphosphinyl]-4-methyl-2-oxo-3-azetidinyl]amino]-2-oxoethylidene]amino]oxy]-2-methylpropanic acid, diphenylmethyl ester, dipotassium salt was dissolved in 1.5 ml of anisole and cooled to 0° C. Trifluoroacetic acid (3 ml) was added, and the resulting mixture was stirred at 0° C. for 2 hours. The volatiles were evaporated, and the residue was triturated with petroleum ether and anhydrous ether to yield a white solid. The solid was dissolved in 2 ml of water and the pH was adjusted to 2.55 with concentrated potassium bicarbonate. This solution was then chromatographed on HP-20 resin (eluting with water, 10% acetone-water, 20% acetone-water, and 40% acetone-water) to yield 100 mg of the title compound.

EXAMPLE 50

[3S(Z)]-[[3-[[(2-Amino-4-thiazolyl)(methoxyimino)acetyl]amino]-2-oxo-1-azetidinyl]phosphonic acid, (2,2-dimethyl-1-oxopropoxy)methyl ester, methyl ester (A)

(S)-[3-[[(Benzyloxy)carbonyl]amino]-2-oxo-1-azetidinyl]phosphonic acid, methyl ester, potassium salt A solution of (S)-3-[(benzyloxy)carbonyl]amino]-2-azetidinone (2.081 g) in 60 ml of dry tetrahydrofuran at −78° C. was treated with 6.25 ml of 1.76 N n-butyl lithium. After 30 minutes, the reaction mixture was added to methyl dichlorophosphate (1.101 ml) in 30 ml of tetrahydrofuran at −78° C. and stirred for 1 hour. The resulting mixture was then poured into a rapidly stirring suspension of 100 ml of pH 6 phosphate and 100 ml of dioxane at 0°. The reaction mixture was stirred at ambient temperature for 1 hour and then placed at 5° C. overnight. Evaporation of the volatiles followed by chromatography on HP-20 resin (eluting with water, 10% acetone-water, 20% acetone-water, 30% acetonewater, and 40% acetone-water) yielded 1.64 g of the title compound.

(B)
(S)-3-[[(Benzyloxy)carbonyl]amino]-2-oxo-1-azetidinyl]phosphonic acid., methyl ester, tetrabutylammonium salt Column chromatography of (S)-[3-[[(benzyloxy)carbonyl]amino]-2-oxo-1-azetidinyl]phosphonic acid, methyl ester, potassium salt with water on Dowex 50X2-400 resin (tetrabutylammonium form) followed by lyophilization yielded 1.89 g of the title compound.

(C)
(S)-[3-[[(Benzyloxy)carbonyl]amino]-2-oxo-1-azetidinyl]phosphonic acid, (2,2,-dimethyl-1-oxopropoxy)methyl ester, potassium salt (S)-[3-[[(Benzyloxy)carbonyl]amino]-2-oxo-1-azetidinyl]phosphonic acid, methyl ester, tetrabutylammonium salt (1.89 g) was dissolved in 68 ml of 1,1,1-trichloroethane. Chloromethyl pivalate (5.39 ml) was added and the resulting mixture refluxed overnight. The volatiles were removed under vacuum. Ion-exchange of the residue by chromatography with water on Dowex 50X2-400 resin (K⊕ form) followed by purification on HP-20 (eluting with water, 10% acetone-water, 20% acetone-water, and 40% acetone-water) yielded 1.36 g of the title compound.

(D)
(S)-[3-[[(Benzyloxy)carbonyl]amino]-2-oxo-1-azetidinyl]phosphonic acid, (2,2-dimethyl-1-oxopropoxy)methyl ester, methyl ester Column chromatography of (S)-[3-[[(benzyloxy)carbonyl]amino]-2-oxo-1-azetidinyl]phosphonic acid, (2,2-dimethyl-1-oxopropoxy)methyl ester, potassium salt with 30% acetone-water on Amberlite IR-116 (H+ form) yielded its conjugate acid, which was dissolved in 50 ml of tetrahydrofuran and cooled to 0° C. Diazomethane was added dropwise to the solution until a light yellow color persisted. The volatiles were removed, and the residue was purified by column chromatography with 50% ethyl acetate-hexane on silica gel to yield the title compound as a mixture of diastereomers (1.04 g).

(E)
[3S(Z)]-[[3-[[(2-Amino-4-thiazolyl)(methoxyimino)acetyl]amino]-2-oxo-1-azetidinyl]phosphonic acid, (2,2-dimethyl-1-oxopropoxy)methyl ester Diisopropylethylamine (0.115 ml) was added to 121 mg (0.6 mmole) of (Z)-2-amino-α-(methoxyimino)-4-thiazoleacetic acid in 2 ml of dimethylformamide at 23° C. The mixture was cooled to −20° C. and diphenyl chlorophosphate (0.125 ml) was added, and the resulting mixture was stirred for 30 minutes to yield a mixed anhydride.

(S)-[3-[[(Benzyloxy)carbonyl]amino]-2-oxo-1-azetidinyl]phosphonic acid, (2,2-dimethyl-1-oxopropoxy)methyl ester, methyl ester (256 mg) was dissolved in 3 ml of dimethylformamide. The benzyloxycarbonyl protecting group was removed by catalytic hydrogenolysis over Pd/C (128 mg). The reaction mixture was placed under nitrogen and cooled to 0° C. Diisopropylethylamine (0.5 ml) was then added to the azetidinone followed by the mixed anhydride. After stirring at 5° C. overnight, the reaction mixture was poured into pH 6 phosphate buffer. The aqueous layer was extracted with ethyl acetate.

The combined ethyl acetate layers were filtered, then washed once with water, once with sodium bicarbonate, and once again with water. The ethyl acetate layer was then dried with $Na_2SO_4$ and solvent was removed in vacuo. Purification of the product by column chromatography on silica gel (eluting with 5% methanol/ethyl acetate) yielded 78 mg of the title compound, melting point 100° C.

What is claimed is:

1. A β-lactam having the formula

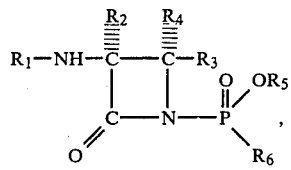

or a pharmaceutically acceptable salt thereof, wherein
$R_1$ is an acyl group derived from a carboxylic acid;
$R_2$ is hydrogen or methoxy;
$R_3$ and $R_4$ are the same or different and each is hydrogen, alkyl, cycloalkyl, phenyl or substituted phenyl, or one of $R_3$ and $R_4$ is hydrogen and the other is alkoxycarbonyl, alken-1-yl, alkyn-1-yl, 2-phenylethenyl, 2-phenylethynyl, carboxyl, —CH$_2$X$_1$ (wherein $X_1$ is azido, amino, hydroxy, alkanoylamino, alkylsulfonyloxy, phenylsulfonyloxy, (substituted phenyl)sulfonyloxy, phenyl, substituted phenyl, halogen, benzylthio, (substituted phenyl)methylthio, triphenylmethylthio, cyano or mercapto), —S—X$_2$ or —O—X$_2$ (wherein $X_2$ is alkyl, phenyl, substituted phenyl, alkanoyl, phenylcarbonyl, (substituted phenyl)carbonyl, or heteroarylcarbonyl), or

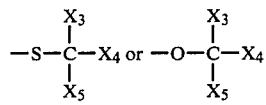

wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano;
$R_5$ is hydrogen, alkyl, substituted alkyl, phenyl, or substituted phenyl; and
$R_6$ is hydroxy, alkoxy, (substituted alkyl)oxy, phenyloxy, (substituted phenyl)oxy, alkyl, substituted alkyl, phenyl, substituted phenyl, heteroaryl, amino, substituted amino, alkylthio, (substituted alkyl)thio, phenylthio, (substituted phenyl)thio, 1-(ethoxycarbonyloxy)ethoxy, 1,3-dihydro-3-oxo-1-isobenzofuranyloxy,

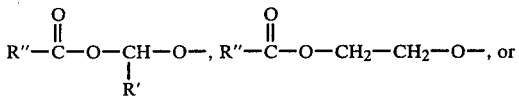

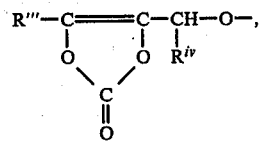

wherein R' is hydrogen or alkyl, R" is alkyl or phenyl, R'" is hydrogen, methyl or phenyl, and $R^{iv}$ is hydrogen or together with R'" is —(CH₂)₃— or —(CH₂)₅—; wherein the terms "alkyl" and "alkoxy" refer to groups having 1 to 10 carbon atoms;

the term "substituted alkyl" refers to an alkyl group substituted with one or more azido, amino, halogen, hydroxy, carboxy, cyano, alkoxycarbonyl, aminocarbonyl, alkoxy, phenyloxy, (substituted phenyl)oxy, (heteroaryl)oxy, mercapto, alkylthio, phenylthio (substituted phenyl)thio, alkylsulfinyl, or alkylsulfonyl groups, the terms "cycloalkyl" refers to groups having 3, 4, 5, 6 or 7 carbon atoms;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms or carboxyl groups;

the terms "alken-1-yl", "alkyn-1-yl" and "alkanoyl" refer to groups having 2 to 10 carbon atoms;

the term "heteroaryl" refers to thienyl, furyl, pyrrolyl, pyridinyl, pyrazolyl, pyrazinyl, thiazolyl, pyrimidinyl or tetrazolyl or one of the above groups substituted with one or more halogen, hydroxyl, nitro, amino, cyano, trifluoromethyl, alkyl of 1 to 4 carbon atoms or alkoxy of 1 to 4 carbon atoms groups;

the term "substituted amino" refers to a group having the formula $-NY_1Y_2$ wherein $Y_1$ is hydrogen, alkyl, phenyl, substituted phenyl, phenylalkyl or (substituted phenyl)alkyl and $Y_2$ is alkyl phenyl, substituted phenyl, phenylalkyl, (substituted phenyl)alkyl, hydroxy, cyano, alkoxy, phenylalkoxy or amino.

2. A β-lactam having the formula

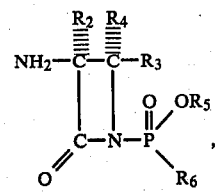

wherein $R_2$ is hydrogen or methoxy;

$R_3$ and $R_4$ are the same or different and each is hydrogen, alkyl, cycloalkyl, phenyl or substituted phenyl, or one of $R_3$ and $R_4$ is hydrogen and the other is alkoxycarbonyl, alken-1-yl, alkyn-1-yl, 2-phenylethenyl, 2-phenylethynyl, halogen, carboxyl, —CH₂X₁ (wherein X₁ is azido, amino, hydroxy, alkanoylamino, alkylsulfonyloxy, phenylsulfonyloxy, (substituted phenyl)sulfonyloxy, phenyl, substituted phenyl, halogen, benzylthio, (substituted phenyl)methylthio, triphenylmethylthio, cyano or mercapto), —S—X₂ or —O—X₂ (wherein X₂ is alkyl, phenyl, substituted phenyl, alkanoyl, phenylcarbonyl, (substituted phenyl)carbonyl, or heteroarylcarbonyl), or

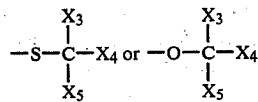

(wherein one of X₃ and X₄ is hydrogen and the other is hydrogen or alkyl, or X₃ and X₄ when taken together with the carbon atom to which they are attached form a cycloalkyl group; and X₅ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano;

$R_5$ is hydrogen, alkyl, substituted alkyl, phenyl, or substituted phenyl; and $R_6$ is hydroxy, alkoxy (substituted alkyl)oxy, phenyloxy, (substituted phenyl)oxy, alkyl, substituted alkyl, phenyl, substituted phenyl, heteroaryl, amino, substituted amino, alkylthio, (substituted alkyl)thio, phenylthio, (substituted phenyl)thio, 1-(ethoxycarbonyloxy)ethoxy, 1,3-dihydro-3-oxo-1-isobenzofuranyloxy,

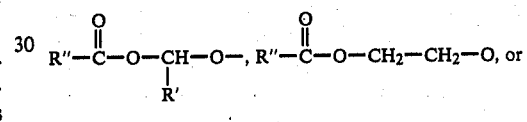

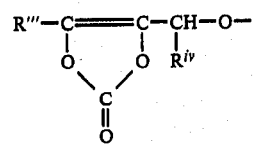

wherein R' is hydrogen or alkyl, R" is alkyl or phenyl, R'" is hydrogen, methyl or phenyl, and $R^{iv}$ is hydrogen or together with R'" is —(CH₂)₃— or —(CH₂)₅—; wherein the terms "alkyl" and "alkoxy" refer to groups having 1 to 10 carbon atoms; the term "substituted alkyl" refers to an alkyl group substituted with one or more azido, amino, halogen, hydroxy, carboxy, cyano, alkoxycarbonyl, aminocarbonyl, alkoxy, phenyloxy, (substituted phenyl)oxy, (heteroaryl)oxy mercapto, alkylthio, phenylthio (substituted phenyl)thio, alkylsulfinyl, or alkylsulfonyl groups, the term "cycloalkyl" refers to groups having 3, 4, 5, 6 or 7 carbon atoms;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms or carboxyl groups;

the terms "alken-1-yl", "alkyn-1-yl" and "alkanoyl" refer to groups having 2 to 10 carbon atoms;

the term "heteroaryl" refers to thienyl, furyl, pyrrolyl, pyridinyl, pyrazolyl, pyrazinyl, thiazolyl, pyrimidinyl or tetrazolyl or one of the above groups substituted with one or more halogen, hydroxyl, nitro, amino, cyano, trifluoromethyl, alkyl of 1 to 4 carbon atoms or alkoxy of 1 to 4 carbon atoms groups;

the term "substituted amino" refers to a group having the formula —NY₁Y₂ wherein Y₁ is hydrogen, alkyl, phenyl substituted phenyl, phenylalkyl or (substituted phenyl)alkyl and Y₂ is alkyl, phenyl, substituted phenyl, phenylalkyl, (substituted phenyl)alkyl, hydroxy, cyano, alkoxy, phenylalkoxy or amino.

3. A β-lactam having the formula

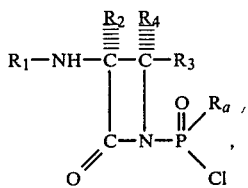

wherein
R₁ is an acyl group derived from a carboxylic acid;
R₂ is hydrogen or methoxy;
R₃ and R₄ are the same or different and each is hydrogen, alkyl, cycloalkyl, phenyl or substituted phenyl, or one of R₃ and R₄ is hydrogen and the other is alkoxycarbonyl, alken-1-yl, alkyn-1-yl, 2-phenylethenyl, 2-phenylethynyl, carboxyl, —CH₂X₁(wherein X₁ is azido, amino, hydroxy, alkanoylamino, alkylsulfonyloxy, phenylsulfonyloxy, (substituted phenyl)sulfonyloxy, phenyl, substituted phenyl, halogen, benzylthio, (substituted phenyl)methylthio, triphenylmethylthio, cyano or mercapto), —S—X₂ or (wherein X₂ is alkyl, phenyl, substituted phenyl, alkanoyl, phenylcarbonyl, (substituted phenyl)carbonyl, or heteroarylcarbonyl), or

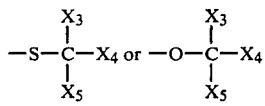

(wherein one of X₃ and X₄ is hydrogen and the other is hydrogen or alkyl, or X₃ and X₄ when taken together with the carbon atom to which they are attached form a cycloalkyl group; and X₅ is formyl alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano; and R_a is alkoxy, (substituted alkyl)oxy, phenyloxy, (substituted phenyl)oxy, alkyl, substituted alkyl, phenyl, substituted phenyl, heteroaryl, alkylthio, (substituted alkyl)thio, phenylthio, (substituted phenyl)thio or

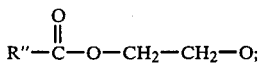

wherein
the terms "alkyl" and "alkoxy" refer to groups having 1 to 10 carbon atoms;
the term "substituted alkyl" refers to an alkyl group substituted with one or more azido, amino, halogen, hydroxy, carboxy, cyano, alkoxycarbonyl, aminocarbonyl, alkoxy, phenyloxy, (substituted phenyl)oxy, (heteroaryl)oxy, mercapto, alkylthio, phenylthio (substituted phenyl)thio, alkylsulfinyl, or alkylsulfonyl groups, the term "cycloalkyl" refers to groups having 3, 4, 5, 6 or 7 carbon atoms;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms or carboxyl groups;

the terms "alken-1-yl", "alkyn-1-yl" and "alkanoyl" refer to groups having 2 to 10 carbon atoms;

the term "heteroaryl" refers to thienyl, furyl, pyrrolyl, pyridinyl, pyrazolyl, pyrazinyl, thiazolyl, pyrimidinyl or tetrazolyl or one of the above groups substituted with one or more halogen, hydroxyl, nitro, amino, cyano, trifluoromethyl, alkyl or 1 to 4 carbon atoms or alkoxy of 1 to 4 carbon atoms groups;

the term "substituted amino" refers to a group having the formula —NY₁Y₂ wherein Y₁ is hydrogen, alkyl, phenyl, substituted phenyl, phenylalkyl or (substituted phenyl)alkyl and Y₂ is alkyl, phenyl, substituted phenyl, phenylalkyl, (substituted phenyl)alkyl, hydroxy, cyano, alkoxy, phenylalkoxy or amino.

4. A compound in accordance with claim 1 wherein R₁ is

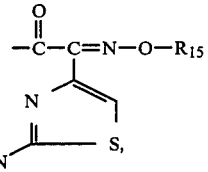

and R₁₅ is methyl, ethyl, carboxymethyl, 1-carboxy-1-methylethyl, 2,2,2,-trifluoroethyl or 2-carboxycyclopropyl.

5. A β-lactam in accordance with claim 1 wherein R₃ and R₄ are the same or different and each is hydrogen, alkyl, cycloalkyl, phenyl or substituted phenyl.

6. A β-lactam in accordance with claim 1 wherein one of R₃ and R₄ is hydrogen and the other is methyl.

7. A β-lactam in accordance with claim 1 wherein R₁ is (Z)-[(2-amino-4-thiazolyl)(methoxyimino)acetyl].

8. A β-lactam in accordance with claim 1 wherein R₁ is (Z)-[(2-amino-4-thiazolyl)](1-carboxy-1-methylethoxy)imino]acetyl].

9. A β-lactam in accordance with claim 1 having the formula

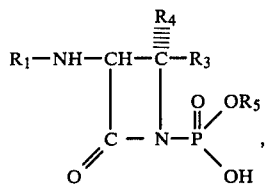

or a pharmaceutically acceptable salt thereof, wherein R₅ is methyl or ethyl.

10. A β-lactam in accordance with claim 9 wherein R₃ and R₄ are the same or different and each is hydrogen, alkyl, cycloalkyl, phenyl or substituted phenyl.

11. A β-lactam in accordance with claim 9 wherein R₃ and R₄ each is hydrogen.

12. A β-lactam in accordance with claim 9 wherein one of R₃ and R₄ is hydrogen and the other is methyl.

13. A β-lactam in accordance with claim 1 having the formula

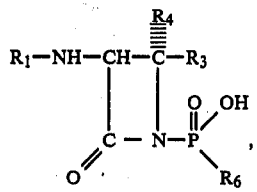

or a pharmaceutically acceptable salt thereof, wherein

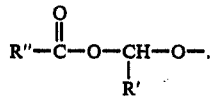

14. The β-lactam in accordance with claim 1, [3S(Z)]-3-[[(2-amino-4-thiazolyl)(methoxyimino)acetyl]amino]-2-oxo-1-azetidinyl]phosphonic acid, methyl ester.

15. The β-lactam in accordance with claim 1, a salt of [3S(Z)]-3-[[(2-amino-4-thiazolyl)(methoxyimino)acetyl]amino]-2-oxo-1-azetidinyl]phosphonic acid, methyl ester.

16. The β-lactam in accordance with claim 1, a salt of [3S(Z)]-2-[[[1-[2-amino-4-thiazolyl)-2-[[1-(hydroxymethoxyphosphinyl)-2-oxo-3-azetidinyl]amino]-2-oxoethylidene]amino]oxy]-2-methyl propanoic acid.

17. The β-lactam in accordance with claim 1, [3S-[3α(Z),4β]]-2-[[[1-(2-amino-4-thiazolyl)-2-[[4-methyl-2-oxo-1-(hydroxymethoxyphosphinyl)-3-azetidinyl]amino]-2-oxoethylidene]amino]oxy]-2-methylpropanoic acid.

18. The β-lactam in accordance with claim 1, a salt of [3S-[3α(Z),4β]]-2-[[[1-(2-amino-4-thiazolyl)-2-[[1-(hydroxyethoxyphosphinyl)-4-methyl-2-oxo-3-azetidinyl]amino]-2-oxoethylidene]-amino]oxy]-2-methylpropanoic acid.

19. The β-lactam in accordance with claim 1, [3S-[-3α(Z),4β]]-2-]]]1-(2-amino-4-thiazolyl)-2-[[1-[[-(2,2-dimethyl-1-oxopropoxy)methoxy]methoxyphosphinyl]-2-methyl-4-oxo-3-azetidinyl]amino]-2-oxoethylidene]amino]oxy]-2-methylpropanoic acid.

20. The β-latam in accordance with claim 1, [3S(Z)]-[[3-[[(2-amino-4-thiazolyl) (methoxyimino)acetyl]amino]-2-oxo-1-azetidinyl]phosphonic acid, (2,2-dimethyl-1-oxopropoxy methyl ester, methyl ester.

21. The β-lactam in accordance with claim 1, a salt of [3S(Z)]-2-]]]1-(2-amino-4-thiazolyl)-2-[[1-(ethoxyhydroxyphosphinyl)-2-oxo-3-azetidinyl]-amino]-2-oxoethylidene]amino]oxy ]-2-methylpropanoic acid.

22. A compound in accordance with claim 1 wherein R₁ is

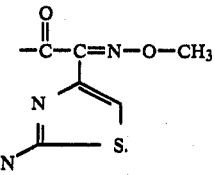

23. A β-lactam in accordance with claim 2 wherein R₂ is hydrogen.

24. A β-lactam in accordance with claim 1 wherein R₁ is

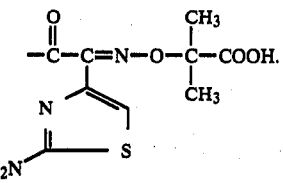

* * * * *

UNITED STATES PATENT OFFICE
CERTIFICATE OF CORRECTION

PATENT NO. : 4,478,749

DATED : October 23, 1984

INVENTOR(S) : William H. Koster et al.

It is certified that error appears in the above-identified patent and that said Letters Patent are hereby corrected as shown below:

Column 1, line 12, "$SO_3^{\oplus}M^{\oplus}$" should be --$SO_3^{\ominus}M^{\oplus}$--.

Column 1, line 17, "$SO_3^{\oplus}M^{\oplus}$" should be --$SO_3^{\ominus}M^{\oplus}$--.

Column 4, before line 15 add:

nocardicin A: Y = -syn(Z)OH
    nocardicin B: Y = -anti(E)OH

Column 18, line 9, "Rhdc" should be --$R_c$--.

Column 24, line 34, "XXIII" should be --XLIII--.

Column 25, line 59, correct the spelling of "in vacuo" by adding a "c".

Column 27, line 53, delete "[b]".

Column 30, lines 63-64, "dicyclohexylcarboiimide" should be --dicyclohexylcarbodiimide--.

*Signed and Sealed this*

*Tenth* Day of *September 1985*

[SEAL]

*Attest:*

DONALD J. QUIGG

*Attesting Officer*    *Acting Commissioner of Patents and Trademarks - Designate*